(12) United States Patent
Chamberlain et al.

(10) Patent No.: US 11,723,624 B2
(45) Date of Patent: Aug. 15, 2023

(54) ULTRASOUND IMAGING SYSTEM WITH AUTOMATIC CONFIGURATION MANAGEMENT AND HINGE MECHANISM

(71) Applicant: FUJIFILM SONOSITE, INC., Bothell, WA (US)

(72) Inventors: Craig Chamberlain, Bothell, WA (US); Patrick Nally, Bothell, WA (US); Ben Dekock, Bothell, WA (US); Gina Kelly, Bothell, WA (US); Roger Swezey, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 338 days.

(21) Appl. No.: 16/203,367

(22) Filed: Nov. 28, 2018

(65) Prior Publication Data

US 2020/0000430 A1 Jan. 2, 2020

Related U.S. Application Data

(60) Provisional application No. 62/716,210, filed on Aug. 8, 2018, provisional application No. 62/690,532, filed on Jun. 27, 2018.

(51) Int. Cl.
*A61B 8/00* (2006.01)
*A61B 8/12* (2006.01)
*A61N 7/02* (2006.01)

(52) U.S. Cl.
CPC .............. *A61B 8/4444* (2013.01); *A61B 8/12* (2013.01); *A61B 8/4254* (2013.01); *A61B 8/54* (2013.01);

(Continued)

(58) Field of Classification Search
CPC ....... A61B 8/0841; A61B 8/12; A61B 8/4254; A61B 8/44; A61B 8/4405; A61B 8/4427;
(Continued)

(56) References Cited

U.S. PATENT DOCUMENTS 9,904,455 B2 * 2/2018 Ban ..................... G06F 3/0481
2009/0093719 A1 * 4/2009 Pelissier ................ A61B 8/465
600/447

(Continued)

FOREIGN PATENT DOCUMENTS

JP 2007097775 4/2007
KR 1020160068632 6/2016

OTHER PUBLICATIONS

International Search Report and Written Opinion for Application No. PCT/US2019/038575 (P004WO), dated Oct. 18, 2019, 12 pages.

(Continued)

*Primary Examiner* — Yi-Shan Yang
*Assistant Examiner* — Alexei Bykhovski
(74) *Attorney, Agent, or Firm* — Womble Bond Dickinson (US) LLP

(57) ABSTRACT

Ultrasound imaging systems for automatically adjusting settings according to an position and/or orientation of one or more interfaces. The ultrasound imaging systems can include a probe configured to send and receive ultrasound signals for performing a medical exam, a medical procedure, or both; and a processor configured to: select a diagnostics mode or a procedural mode based on an operating orientation of the ultrasound imaging system or a portion thereof, and adjust one or more settings of the imaging system according to the selected diagnostics mode or the selected procedural mode.

13 Claims, 16 Drawing Sheets

(52) U.S. Cl.
CPC ........... *A61B 8/4477* (2013.01); *A61B 8/4483* (2013.01); *A61B 8/461* (2013.01); *A61N 7/02* (2013.01)

(58) Field of Classification Search
CPC ... A61B 8/4444; A61B 8/4477; A61B 8/4483; A61B 8/461; A61B 8/467; A61B 8/54; A61N 7/02
See application file for complete search history.

(56) References Cited

U.S. PATENT DOCUMENTS

| | | | | |
|---|---|---|---|---|
| 2009/0187102 | A1* | 7/2009 | Di Marco | A61B 8/462 600/437 |
| 2010/0286519 | A1* | 11/2010 | Lee | A61N 7/02 600/439 |
| 2013/0172757 | A1 | 7/2013 | Frigstad et al. | |
| 2013/0342579 | A1* | 12/2013 | Yu | G09G 5/34 345/649 |
| 2014/0121489 | A1 | 5/2014 | Kommu Chs | |
| 2014/0378833 | A1 | 12/2014 | Cheng et al. | |
| 2015/0359515 | A1 | 12/2015 | Han | |
| 2016/0120507 | A1 | 5/2016 | Ninomiya et al. | |
| 2018/0146499 | A1 | 5/2018 | Jun | |
| 2018/0153513 | A1* | 6/2018 | Mauldin, Jr. | A61B 8/463 |
| 2019/0261846 | A1* | 8/2019 | Oh | A61B 1/0002 |
| 2020/0281565 | A1* | 9/2020 | Yee | G16H 30/20 |

OTHER PUBLICATIONS

International Preliminary Report and Written Opinion on the Patentability of Application No. PCT/US2019/038575, dated Jan. 7, 2021, 9 pages.

Extended European Search Report on the Patentability of Application No. 19824471.7-1126/3813671 dated Feb. 16, 2022, 10 pages.

* cited by examiner

ULTRASOUND IMAGING SYSTEM WITH AUTOMATIC CONFIGURATION MANAGEMENT AND HINGE MECHANISM

CROSS-REFERENCE TO RELATED APPLICATION(S)

This application claims the benefit of and priority to U.S. Provisional Patent Application No. 62/690,532, filed on Jun. 27, 2018, which is incorporated by reference herein in its entirety. This application also claims the benefit of and priority to U.S. Provisional Patent Application No. 62/716,210, filed on Aug. 8, 2018, which is incorporated by reference herein in its entirety.

TECHNICAL FIELD

The disclosed technology relates to ultrasound imaging systems, and in particular to systems for automatic configuration management.

BACKGROUND

In ultrasound imaging, an operator of a system uses a probe to obtain ultrasound images of a patient during an examination or a procedure. Some ultrasound imaging systems can support both diagnostics and procedural modes. The diagnostic modes image and measure internal body tissue or flows while procedural mode aid in minimally invasive procedures, such as delivery of anesthesia. In certain scenarios, such as in emergency room applications, such dual purpose ultrasound imaging systems can be used to conduct multiple different types of procedures in a relatively short amount of time.

Configuring the ultrasound imaging system to support different types of examinations/procedures can reduce the number of special purpose machines required in an already-crowded hospital setting. However, such multi-use systems can also increase the burden on the operator to be familiar with multiple different settings, commands, user-interfaces, etc. required for each type of examination and procedure. The increased burden can lead to mistakes, especially in fast-paced settings. This problem can be further exemplified during procedural applications, where the individual operating the ultrasound imaging system often cannot easily control or adjust its settings. For example, in performing a procedure, such as a needle biopsy, such an individual is often forced to use one hand to manipulate a medical instrument, such as a needle, and the other hand to operate an ultrasound probe to track the medical instrument. As a result, the care provider cannot easily interact with the ultrasound imaging system and often has to rely on a second person, who may not be familiar with the system, to assist in controlling the system settings.

DETAILED DESCRIPTION

Figure 1B:
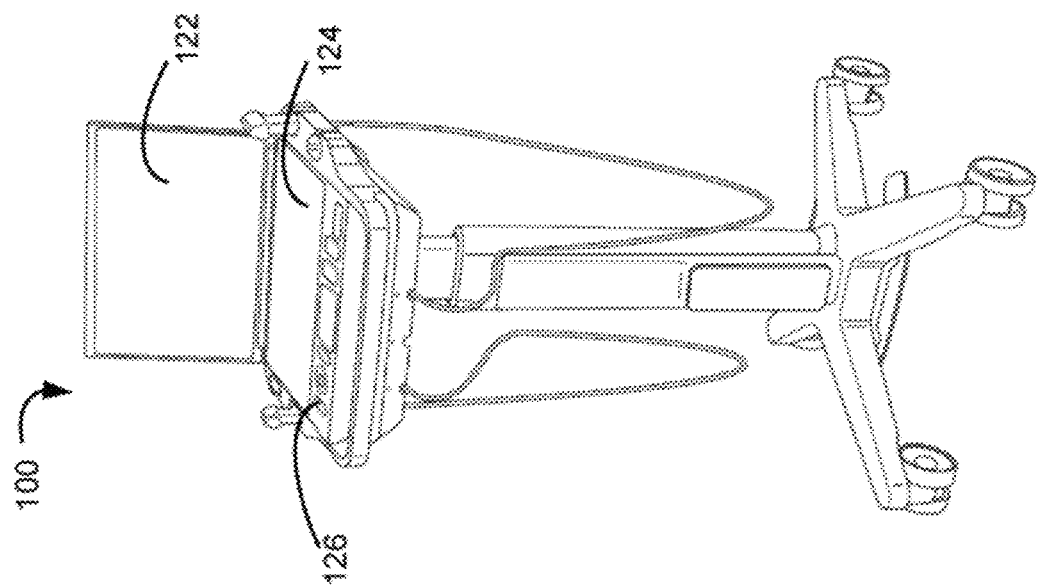
FIG. 1B is an isometric view of the ultrasound imaging system in a first operating configuration in accordance with an embodiment of the present technology.

Specific details of several embodiments of ultrasound imaging systems for automatically managing configurations and settings, and associated devices and methods, are described below reference to FIGS. 1A-16. In some embodiments, for example, an ultrasound imaging system can be configured to operate in a diagnostics mode or a procedural mode based at least in part on a detected position or orientation of one or more user interfaces. In one embodiment, the ultrasound imaging system can operate according to a specific mode or setting based on an position of a first interface (e.g., a display screen or a touch screen), a second interface (e.g., a display screen or a touch screen, a tactile interface unit, etc.), and an angle between the interfaces. Note that the techniques disclosed herein are not limited to setting or selecting a mode based on the position or orientation of one or more interfaces, and can be applied to the positions and orientation of other parts of the ultrasound imaging system, such as, for example, a docking tray, etc.

To change operating modes between a diagnostics mode or a procedural mode, or a specific examination/procedural mode, the ultrasound imaging system adjusts one or more settings. For example, the ultrasound imaging system adjusts one or more probe or ultrasound parameter settings (e.g., imaging mode, gain, focal depth, frequency, etc.), control display settings, input/control sensitivity, etc. according to the detected orientation of the user interfaces with respect to each other. In one embodiment, the ultrasound imaging system adjusts between two different types of procedure modes or diagnostic modes in response to detected positions or orientation of the user interfaces or other parts of the ultrasound imaging system.

In some embodiments, for example, the ultrasound imaging system can include a hinge mechanism that is configured to allow the user to change the position or the orientation of the one or more user interfaces. In one embodiment, the hinge mechanism (e.g., a pin joint) can be located in front of a column of a stand instead of directly over the stand and directly under a center of gravity point of the user interface device. The hinge mechanism is enclosed within hinge covers to reduce any potential impingement of operator's hands during operation. The hinge mechanism includes an upper tilt stop and a lower tilt stop within the hinge covers. In one embodiment, the hinge mechanism can include electric circuits (e.g., switch, position detector, accelerometer, etc.) configured to determine the position/orientation of the user interfaces.

In one embodiment, the hinge mechanism includes a clutch configured to provide different resistances to different movement directions. For example, the clutch mechanism can include a spring-based compression design that can increase/decrease a friction force between adjacent moving members. In another embodiment, the clutch mechanism can include a wrap-spring design that can provide a different resistance/friction force according to a direction, a size, a tightness, etc. of a spring winding. Also, the clutch mechanism can include a release mechanism to provide forces against a direction of the winding (e.g., unwind) in the wrap-spring design.

In one embodiment, the hinge mechanism is accompanied by a base mechanism configured to mechanically operate or interact with the hinge mechanism located in front of the column of the stand. For example, the hinge mechanism can extend further in a forward direction from the column than a backward direction. In some embodiments, the front portion of the base mechanism extends beyond the center of gravity point of the user interface device.

Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology. The phrases "in some embodiments," "according to some embodiments," "in certain embodiments," "in the illustrated embodiment," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

Figure 1A:
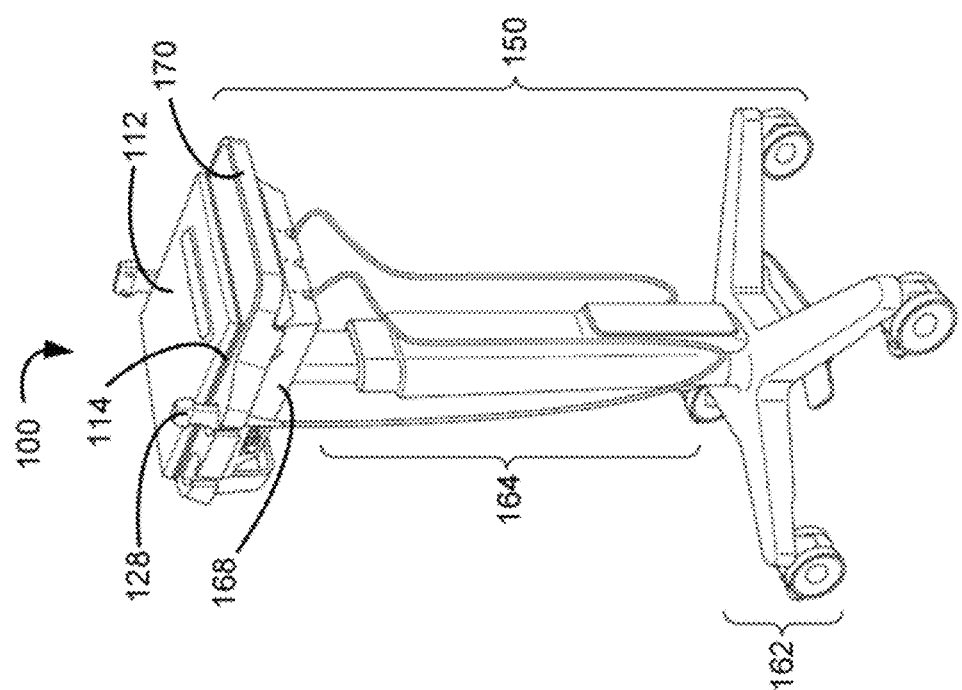
FIG. 1A is an isometric view of a representative ultrasound imaging system in a storage configuration in accordance with an embodiment of the present technology.

FIGS. 1A and 1B show a representative ultrasound imaging system 100 that implements the present technology for alternating between different operating modes in a medical environment depending on the detected orientation or position of parts (such as, for example, but not limited to, the docking tray or housing receptacle) of the ultrasound imaging system 100. In one embodiment, the ultrasound imaging system 100 is a cart-based system that includes an imaging unit removably connected to an adjustable stand. The imaging unit is configured to image human or animal subjects, by sending ultrasound signals or pulses into the target (e.g., the patient's body), receiving reflected echo signals/pulses, and processing the received reflections.

In some embodiments, the imaging unit includes a first interface that is rotatably connected to a second interface, such that a relative angle or orientation between the two interfaces can be changed. For example, in some embodiments, the first and second interfaces are connected through a pin or a hinge joint, such that the first interface and the second interface rotate about an axis corresponding to the joint. In some embodiments, the ultrasound imaging system 100 switches between supported modes according to the relative location, angle, or orientation of the two interfaces. In alternative embodiments, the ultrasound imaging system 100 switches between supported modes according to the relative location, angle, or orientation of one interface with respect to another part of the ultrasound imaging system 100 or a plane defined with respect to the ultrasound imaging system 100, or a part thereof.

In some embodiments, the ultrasound imaging system 100 supports diagnostic imaging modes and one or more procedural modes performed by a medical professional. During a diagnostic examination, the medical professional(s) and/or the operator can use the ultrasound imaging system 100 to passively observe a physiological region of the patient. For example, ultrasound examinations can include one or more of cardiac imaging, abdominal imaging, pelvic imaging, obstetric imaging, Focused Assessment with Sonography in Trauma (FAST) exams, etc.

In comparison, during a procedure, the medical professional(s) and/or the operator uses the ultrasound imaging system 100 to image/track progress while actively performing a medical procedure on a physiological region of the patient to achieve a specific task (e.g., a nerve block). Procedures, in general, can require puncturing of the patient's skin or otherwise inserting a device into the patient's body. Some example examinations and/or procedures can include applications in anesthesiology, angiology, cardiology, emergency medicine, various surgeries, gynecology/obstetrics, otolaryngology, neonatology, ophthalmology, pulmonology, urology, etc. For example, ultrasound-based procedures can include trauma or emergency procedures (e.g., bullet removal or sutures), anesthetic procedures (e.g., perform a nerve block), PICC line procedures, etc.

The ultrasound imaging system 100 is configured to operate in different modes that correspond to the various objectives/scenarios. In some embodiments, the ultrasound imaging system 100 operates in a diagnostics mode and a procedural mode that support one or more diagnostic examinations and one or more procedures, respectively.

In supporting the diagnostic examinations, the ultrasound imaging system 100 operates in a diagnostics mode by target monitoring of the patient's body/tissue. For example, the imaging system processes the received reflections to present a visual depiction of the examined portion of the patient's body. In processing the received reflections, the ultrasound imaging system 100 converts characteristics of the received echo signals (e.g., their amplitude, phase, power, frequency shift, etc.) into data that are quantified and displayed for the user as an image that represents tissue, bone, blood, etc. of the patient's body in the examined region.

During many diagnostic examinations, the medical professionals face the ultrasound imaging system 100 to view the progress/images while manipulating a probe that sends the ultrasound signals and/or receives the reflections. The medical professional can keep one hand on a device interface (e.g., a keyboard, a mouse, a button, etc.) during the examination or periodically use both hands to control the ultrasound imaging system 100. As such, in the diagnostics mode, the ultrasound imaging system 100 can be configured to provide a larger set of controls, to allow the operator to fine tune the imaging parameters, take measurements from captured images, freeze images, capture images, create reports, etc.

In supporting the procedures, the ultrasound imaging system 100 operates in a procedural mode by monitoring the location of medical devices/instruments in relation to the patient's body/tissue. For example, in one embodiment, in the procedural mode, the ultrasound imaging system 100 displays representations of procedural equipment (e.g., needle, stent, catheter/tube, robotic device, etc.) and/or injected material (e.g., contrast, anesthetic, medicine, etc.) relative to an imaged area of the patient's body. Also, in one embodiment, in a procedure mode, the ultrasound imaging system 100 tracks a position, a location, an orientation, etc. of the medical instrument inside a patient's body during the medical procedure.

During many procedures using the ultrasound imaging system 100, the medical professional performing a medical procedure is often further away (i.e., in comparison to the diagnostic examinations) from the ultrasound imaging system 100 and/or with the patient located between the medical professional and the interfaces. Further, during the medical procedures, both hands of the medical professional are often occupied, with one holding the procedural equipment and the other holding the ultrasound probe. As such, in one embodiment, in a procedural mode, the ultrasound imaging system 100 highlights or enhances buttons or portions of the GUI (i.e., GUI portions) that are necessary or often-accessed and/or reduce or eliminate less-accessed features. In some embodiments, if the ultrasound imaging system 100 includes multiple displays (e.g., a top screen and a bottom screen), the displayed representation utilizes multiple screens, such as by having one large image extending across multiple interfaces/screens, displaying different zoom levels on each interface/screen, displaying a full-size color image and full-size black and white image on different screens, etc. Often, a GUI used during procedural mode will have fewer controls on it because a user is more interested in performing the procedure than optimizing imaging parameters.

To provide seamless support of multiple modes, the ultrasound imaging system 100 is configured to switch between modes based on detecting an orientation or a position of one or more portions of the system (e.g., an interface, a docking tray, etc.). Accordingly, the ultrasound imaging system 100 allows the user to change between operating modes by changing the orientation or the position of the one or more portions of the ultrasound imaging system. For example, in some embodiments, the operator uses a handle to rotate a docking tray, a bottom interface, a top interface, etc. about an adjustable hinge. In response, the ultrasound imaging system detects the change in orientation/position and uses the detected position to alternate between different operating modes, such as between the diagnostics mode and the procedural mode.

In some embodiments, a stand for the ultrasound imaging system 100 includes an adjustable hinge configured to facilitate the multiple orientations/positions, and thereby the different operating modes. In at least one embodiment, the adjustable hinge is located in front of a column that supports the imaging unit and/or the docking tray. In one embodiment, the adjustable hinge is further configured to provide different levels of resistance to movement based on a variety of factors, such as a direction of force applied by the operator, a control input from the operator, etc. In one embodiment, the adjustable hinge includes a clutch mechanism configured to provide different levels of resistance according to one or more of a user-operated lever/button, a direction of force or movement, or a combination thereof.

FIG. 1A is an isometric view of a representative ultrasound imaging system 100 in a storage configuration in accordance with an embodiment of the present technology. In some embodiments, the ultrasound imaging system 100 is a conventional clam-shell design with a lid 112 including a display screen (shown closed) and a base portion 114 including processing electronics, power supply, fans, etc. (not shown). The ultrasound imaging system 100 is mounted on a stand 150 with a tilt adjustment as will be explained below. For the storage configuration, the lid 112 can be rotated about a hinge axis and positioned relatively parallel and over the base portion 114. A resulting angle between the two portions can be effectively 0°. In the storage configuration, in one embodiment, the ultrasound imaging system 100 turns off, deactivates, modifies, etc. one or more portions or functionalities thereof, or a combination thereof based on the position and orientation of the imaging system. For example, the ultrasound imaging system 100 turns off or deactivates one or more displays, signal generators, input keys/controllers, software processes, etc.

FIG. 1B is an isometric view of the ultrasound imaging system 100 in a first operating configuration in accordance with an embodiment of the present technology. In some embodiments, the imaging unit includes the lid 112 of FIG. 1A (including e.g., a display screen, a touch screen, etc.) opened with respect to the base portion 114 of FIG. 1A in an operating configuration. The ultrasound imaging system 100 is connected to one or more probes 128 of FIG. 1A that the operator can use to direct ultrasound signals or pulses into the patient's body, and to receive reflected echo signals/pulses. For example, the received reflections are processed to present a visual depiction of the examined portion of the patient's body and/or medical instruments, such as during a diagnostic exam.

In some embodiments, the imaging unit (e.g., the lid 112, the base portion 114, etc.) is attached to the stand 150 of FIG. 1A. The stand 150 includes a column 164 that extends upward from a base 162 (e.g., a wheeled base). The stand 150 further includes a docking tray 168 connected to a top portion of the column 164. The docking tray 168 removably connects to/receives the imaging unit, such as by connecting to and receiving the base portion 114. In some embodiments, the docking tray 168 includes a handle 170 that an operator can grasp to move/displace the ultrasound imaging system 100 and/or orient/position the docking tray 168 and/or the base portion 114.

In some embodiments, an adjustable hinge connects the docking tray 168 to the column 164 and allows the docking tray 168 and a bottom/docked portion of the imaging unit (e.g., the base portion 114 and/or an interface thereon) to rotate relative to a horizontal plane. In one embodiment, the adjustable hinge fixes or holds the docking tray 168 at multiple angles with respect to a horizontal plane. For example, in one embodiment, the adjustable hinge is a barrel-type hinge that includes position stops that limit a range (e.g., between 0-90° below horizontal) of motion/angles for docking tray 168. Other ranges could also be selected based on user/design specifications. For example, in one embodiment, the adjustable hinge includes one or more adjustable motion stops that the user can reposition. Also, in one embodiment, the adjustable hinge includes one or more motion stops that correspond to a specified/designated range of motion. In one embodiment, the hinge has a locking mode (e.g., when a clutch is engaged) that increases the force required to move the hinge so that the imaging system will not change orientation due to gravity, but can easily move to a new orientation if desired. In one embodiment, the hinge includes a button or a lever activated by the weight of the docking tray 168 thereby activating the locking mode. The button or the lever can disengage when the user grabs or lifts the handle 170 or based on the user's manipulation of the clutch mechanism.

To change the operating mode of the imaging system, in one embodiment, the two interfaces are positioned to create an angle in two or more angular ranges. For example, in one embodiment, a medical professional rotates a bottom interface about the horizontal plane to change the operating mode between a diagnostics mode and a procedural mode. In some embodiments, the ultrasound imaging system 100 operates in a diagnostics mode when the lid 112 is in an open position and the base portion 114 is oriented at an angle between 0-55° below horizontal and a procedural mode when the angle is greater than 55° below horizontal. Other angles could also be selected based on the stand of the base portion or could be user-defined.

In some embodiments, the adjustable hinge is positioned in front of the column 164. Since a medical professional would face the ultrasound imaging system 100, more components (e.g., one or more interface portions, probes, circuit components, etc.) can be located toward a front portion of the system for accessibility. Further, in some embodiments, the medical professional can grab a front portion of the system to adjust the orientation, by applying a rotational force from the front. Accordingly, to keep the system stable during usage, the column is located behind (i.e., away from the user operating/facing the imaging unit) a center of gravity of the imaging unit and/or the docking tray 168 while adjustable hinge is located below the center of gravity and in front of the column 164. In comparison to having the adjustable hinge co-linear with and directly over the column 164, the above described location of the adjustable hinge increases stability during movement and orientation changes.

In some embodiments, the adjustable hinge includes a clutch mechanism configured to control resistance/friction levels required to move the docking tray 168 and the imaging unit. For example, the clutch mechanism can be configured to provide multiple resistance/friction levels for different directions of movement (e.g., orientation changes of the docking tray 168). The clutch mechanism provides a first resistance level when a user tilts (e.g., rotates about rotational axis of the adjustable hinge) the docking tray 168 upwards, and a second resistance level when the user tilts the docking tray 168 downwards. Also for example, in one embodiment, the clutch mechanism is attached to a control mechanism (e.g., a handle, a lever, a foot pedal, a button, etc.) that is configured to engage and disengage the clutch mechanism according to user manipulation. In one embodiment, the clutch mechanism is configured to provide varying amounts of resistance/friction levels according to the control mechanism, such as force applied thereon or a position thereof. For some embodiments, the clutch mechanism includes a wrap-spring clutch where the tightness of a wound spring can be relieved based on the position of the control mechanism. Further the winding direction provides differing levels of resistance according to different direction (e.g., upward or downward movement at the handle 170) of orientation changes or the direction of the corresponding force. For some embodiments, the clutch mechanism includes a set of plates that are compressed together with differing levels of force according to the control mechanism. Details of the adjustable hinge are described below.

Figure 2B:
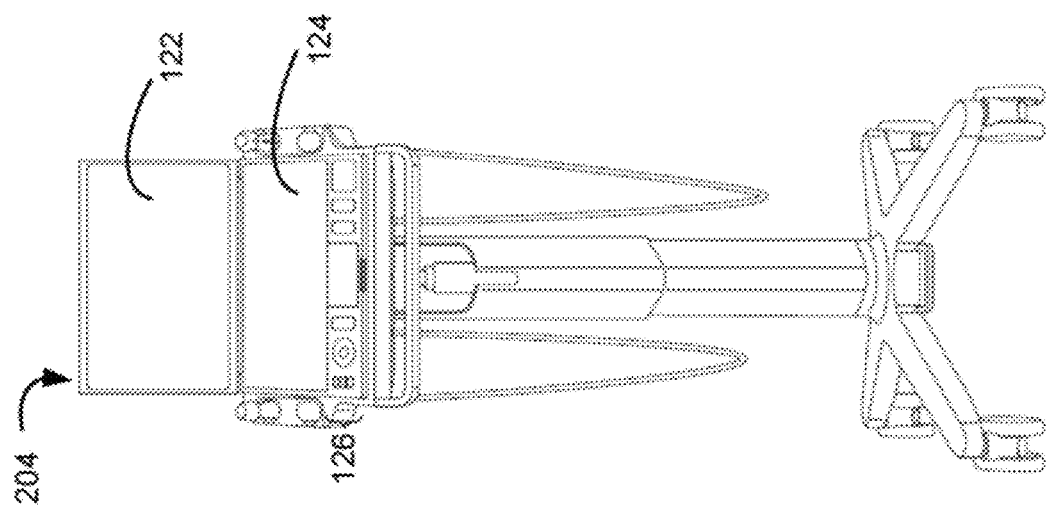
FIG. 2B is a front view of the ultrasound imaging system in a second operating configuration in accordance with an embodiment of the present technology.
Figure 2A:
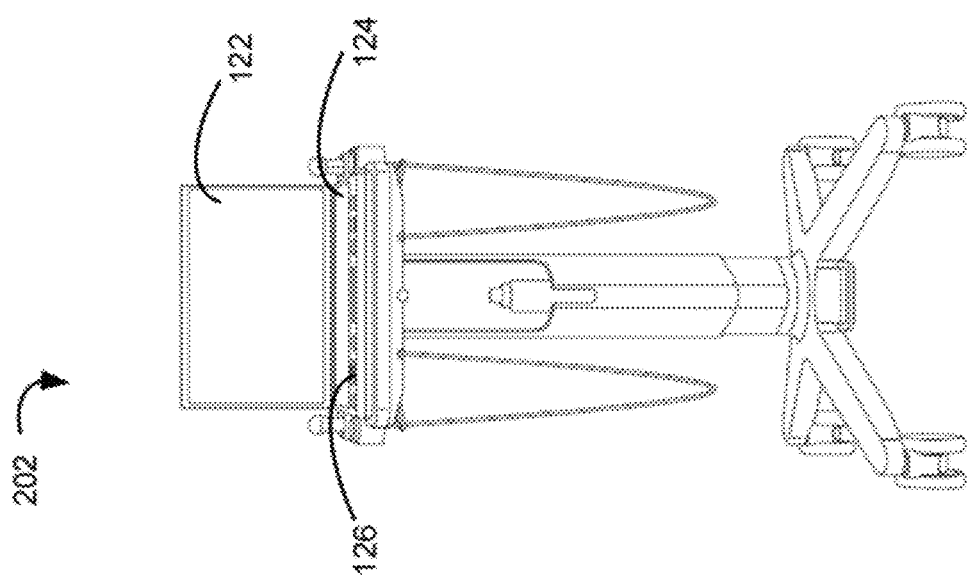
FIG. 2A is a front view of the ultrasound imaging system in a first operating configuration in accordance with an embodiment of the present technology.

FIGS. 2A-2B, 3A-3B, and 4A-4B illustrate various aspects of the ultrasound imaging system 100 of FIG. 1A and FIG. 1B in different representative operating configurations in accordance with an embodiment of the present technology. For example, FIG. 2A is a front view of the ultrasound imaging system 100 in a first operating configuration 202 (e.g., the diagnostics mode) in accordance with an embodiment of the present technology. FIG. 2B is a front view of the ultrasound imaging system 100 in a second operating configuration 204 (e.g., the procedural mode) in accordance with an embodiment of the present technology.

The first operating configuration 202 and the second operating configuration 204 can each correspond to different orientations of the imaging system, such as an orientation or a position of one or more of the interfaces, an angle between the first interface 122 and the second interface 124, a height or length of the column 164 of FIG. 1, etc. In some embodiments, the first operating configuration 202 corresponds to an orientation of the second interface 124 and/or the docking tray 168 at a top portion of a range of motion (e.g., closest to being parallel with a horizontal plane) or to a range of positions including the top position, and the second operating configuration 204 corresponds to an orientation of the second interface 124/the docking tray 168 at a bottom position (e.g., furthest away from the horizontal plane and/or closest to being parallel to a vertical plane) or to a range of positions including the bottom position. Comparatively, the first operating configuration 202 corresponds to a smaller angular deviation of the docking tray 168 or the second interface 124 from a horizontal plane than the second operating configuration 204.

In one embodiment, the ultrasound imaging system 100 detects the operating configuration (e.g., the orientation of the second interface 124, the docking tray 168, etc.) and initiates various corresponding modes (e.g., the diagnostics mode, the procedural mode, etc.). For example, in some embodiments, the ultrasound imaging system 100 (e.g., the imaging device, the docking tray 168, the adjustable hinge, etc.) includes an accelerometer, a gyroscope, a position encoder, a switch, etc. configured to detect the orientation of the imaging unit, height of the imaging system, or a change thereof. Based on the detection, a processor in the ultrasound imaging system 100 is programmed to use the first operating configuration 202 to trigger implementation of the diagnostics mode, and the second operating configuration 204 to trigger implementation of the procedural mode. In some embodiments, the ultrasound imaging system 100 implements the different modes by adjusting one or more of the probes or ultrasound signal settings (e.g., imaging mode, B-mode, Doppler, color flow, the gain, the focal zone, the signal frequency, etc.), controlling display settings (e.g., location/size/color of the visual depiction, controlling the presence or location of ultrasound imaging system controls on a GUI, settings/status, etc.), adjusting input/control sensitivity (e.g., touch/pressure sensitivity, change rate/magnitude, etc.), etc.

Figure 3B:
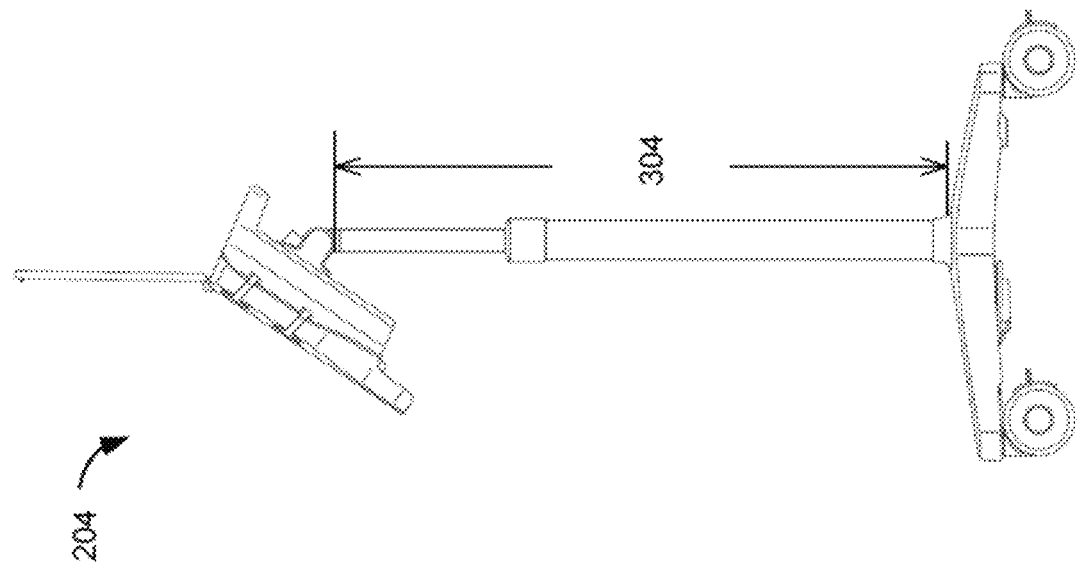
FIG. 3B is a profile view of the ultrasound imaging system in the second operating configuration in accordance with an embodiment of the present technology.
Figure 3A:
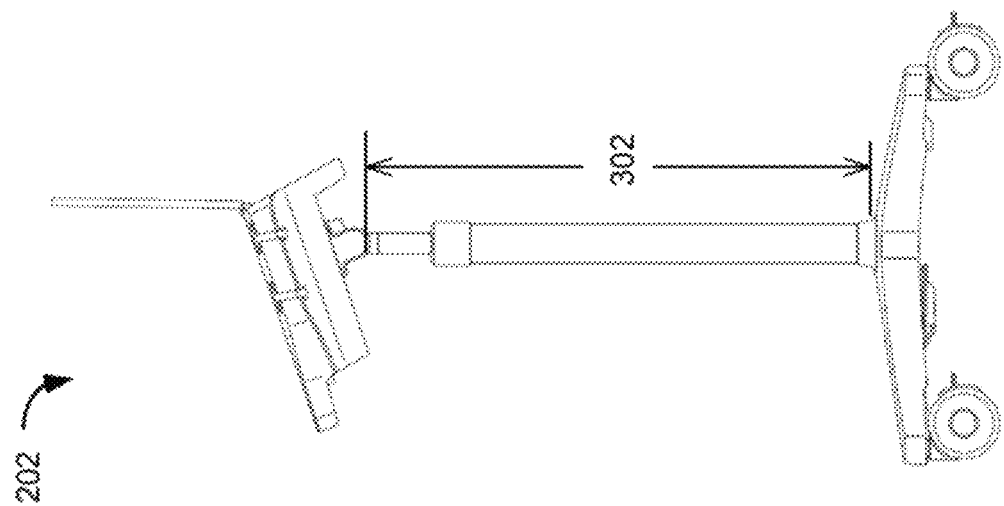
FIG. 3A is a profile view of the ultrasound imaging system in the first operating configuration in accordance with an embodiment of the present technology.

FIG. 3A is a profile view of the ultrasound imaging system 100 in the first operating configuration 202 in accordance with an embodiment of the present technology. FIG. 3B is a profile view of the ultrasound imaging system 100 in the second operating configuration 204 in accordance with an embodiment of the present technology. As illustrated in FIGS. 3A and 3B, in one embodiment, the first operating configuration 202 (e.g., the diagnostics mode) is selected by the detected height (e.g., a distance between the base portion 162 and the adjustable hinge/top of the vertical portion) of the imaging system with a first height 302 being used for a diagnostic procedure and the second operating configuration 204 (e.g., the procedural mode) being selected when the imaging system is at a second height 304. In some embodiments, the first height 302 is less than the second height 304.

Figure 4B:
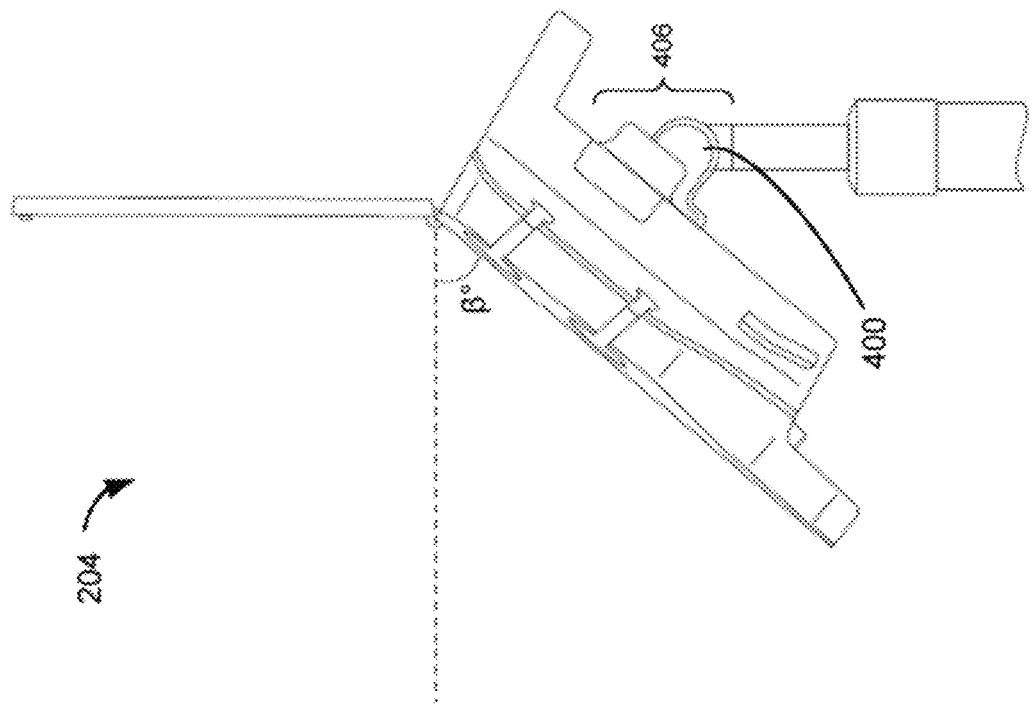
FIG. 4B is a profile view of the top portion of the ultrasound imaging system in the second operating configuration in accordance with an embodiment of the present technology.
Figure 4A:
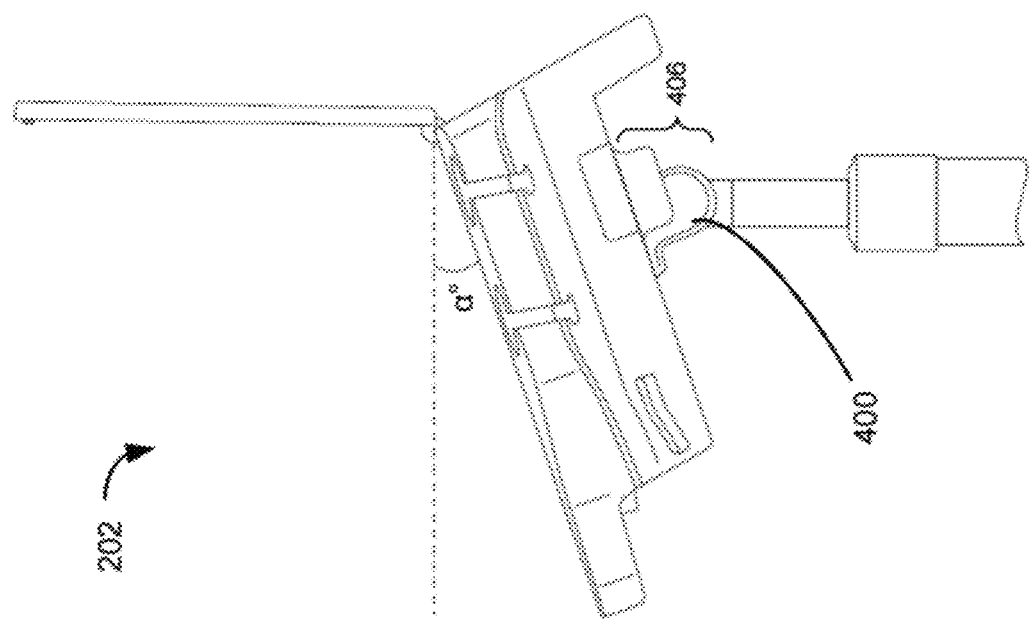
FIG. 4A is a profile view of a top portion of the ultrasound imaging system in the first operating configuration in accordance with an embodiment of the present technology.

FIG. 4A is a profile view of a top portion of the ultrasound imaging system 100 in the first operating configuration 202 in accordance with an embodiment of the present technology. FIG. 4B is a profile view of the top portion of the ultrasound imaging system 100 in the second operating configuration 204 in accordance with an embodiment of the present technology.

As discussed above, in some embodiments, the operator changes/sets the orientation of the ultrasound imaging system 100 (e.g., the base portion 114 of FIG. 1, the second interface 124 of FIG. 1, the docking tray 168 of FIG. 1, etc.). For example, in one embodiment, the operator uses the handle 170 of FIG. 1 to rotate the docking tray 168 about an adjustable hinge 400 attached to a tilt mechanism 406 located near the top of the stand column 164 of FIG. 1 to orient/position the ultrasound imaging system 100 to change the operating configuration of the system.

In some embodiments, the adjustable hinge 400 allows the docking tray 168 to rotate between 0° (horizontal) or some positive angle to minus 90° (vertical) as measured in reference to a horizontal plane. For example, in one embodiment, the adjustable hinge 400 allows the docking tray 168 and/or the second interface 124 to rotate from 15° below the horizontal plane, such as for the first operating configuration 202 of FIG. 2, to 55° or more below the horizontal plane, such as for the second operating configuration 204. In one embodiment, the first operating configuration is selected when the ultrasound imaging system 100 (e.g., the base portion 114 and/or the second interface 124 therein) is in a first orientation, such as for a laptop computer or a clamshell device, and the second operating configuration 204 is selected when the second interface of the ultrasound imaging system 100 is in a second orientation, such as a vertical or near vertical arrangement between the interfaces, such as similar to a flat surface of a tablet computer.

As illustrated in FIGS. 4A and 4B, in one embodiment, the first operating configuration 202 (e.g., orientation/angle corresponding to the diagnostics mode) corresponds to a smaller angular deviation of the docking tray 168 or the second interface 124 from a horizontal plane than the second operating configuration 204 (corresponding to the procedural mode). For example, the first operating configuration 202 corresponds to a first angle ($\alpha$) of 0° to −45° between the base portion 114 and the horizontal plane. Also, the second operating configuration 204 corresponds to a second angle ($\beta$) of −46° to −90° between the base portion 114 and horizontal. In some embodiments, the range of angles used to define the first operating configuration and the second operating condition need not be the same. For example, in one embodiment, the first range of angles for defining the first operating configuration is a range of angles including or about 0° to −15°, while the second range of angles defining the second operating configuration is −16° to −55°.

Figure 5:
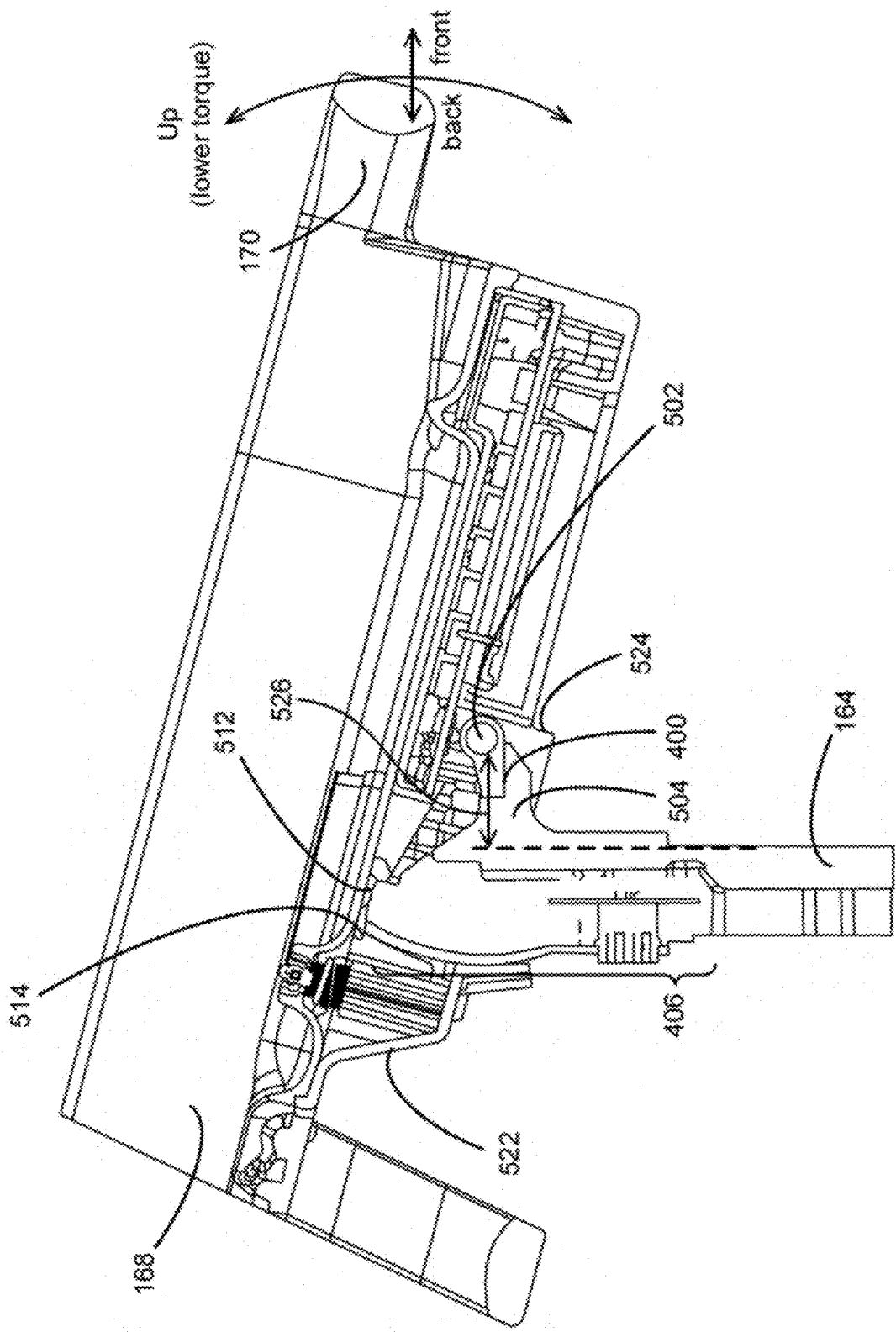
FIG. 5 is a cross sectional view of a tilt mechanism at the top of the column in accordance with an embodiment of the present technology.

FIG. 5 is a cross sectional view of a tilt mechanism 406 at the top of the column 164 in accordance with an embodiment of the present technology. In one embodiment, the tilt mechanism 406 includes a top portion of the adjustable stand 150 of FIG. 1 and connects to or is integral with the adjustable hinge 400. In one embodiment, the tilt mechanism 406 and/or the adjustable hinge 400 includes a pivot pin 502 (e.g., a pin/pivot providing an axis of rotation for the adjustable hinge 400) in front of the column 164 (i.e., instead of directly over/on top of the column 164) and a hinge platform 504 extending away from the column 164 along a horizontal direction. In some embodiments, the hinge platform 504 functions as an arm that extends away from the column 164 and provides support (e.g., bearing the weight) for the docking tray 168, the imaging unit, etc. that are attached through the adjustable hinge 400. Accordingly, the length of hinge platform 504 provides a horizontal separation distance 526 between the column 164 and the pivot pin 502 (e.g., the axis of rotation for the adjustable hinge 400).

The hinge platform 504 extends horizontally from the column 164 and attached to, and integral with, the adjustable hinge 400, thereby providing increased stability for the ultrasound imaging system 100. In one embodiment, the hinge platform 504 and the adjustable hinge 400 places the axis of rotation (e.g., the location of the pivot pin 502) in front of the column 164 of the adjustable stand 150 and closer to an operator. Using the hinge platform 504, in one embodiment, the axis of rotation is placed below a center of mass for the imaging unit, the docking tray 168, and/or the probes 128. Further, the column 164 is located behind the axis of rotation to reduce the possibility of the ultrasound imaging system 100 of tipping backwards during transport (e.g., due to pushing the ultrasound imaging system 100 backwards) or during change in orientation (e.g., due to upward rotation of the docking tray 168 or corresponding force at the handle 170).

In one embodiment, the tilt mechanism 406 further includes an upper tilt stop 512 and a lower tilt stop 514 enclosed within a first hinge cover 522 and a second hinge cover 524. The first hinge cover 522 extends from a bottom portion/surface of the docking tray 168 along a downward direction and cover/contact a back surface of the tilt mechanism 406. In one embodiment, the second hinge cover 524 extends from a bottom portion/surface of the docking tray 168 and cover/contact a front surface of the tilt mechanism 406. In one embodiment, the first hinge cover 522 and the second hinge cover 524 encloses the adjustable hinge 400, the upper tilt stop 512, the lower tilt stop 514, etc. Accordingly, the first hinge cover 522 and the second hinge cover 524 provide improved usability and safety for the ultrasound imaging system 100. By covering the adjustable hinge 400, the upper tilt stop 512, the lower tilt stop 514, etc., the first hinge cover 522 and the second hinge cover 524 can reduce impingement of user's hand/fingers during operation of the ultrasound imaging system 100.

In one embodiment, the upper tilt stop 512 and the lower tilt stop 514 provide limits on upward rotation and downward rotation, respectively, of the docking tray 168. For example, as illustrated in FIG. 4, in one embodiment, the upper tilt stop 512 comprises a surface or an edge at the top of the tilt mechanism 406 that is configured to contact a bottom portion/surface of the docking tray 168. Also, as illustrated in FIG. 5, in one embodiment, the lower tilt stop 514 comprises a notch or a protrusion connected to/integral with the top of the tilt mechanism 406 that is configured to contact the first hinge cover 522.

Figure 6:
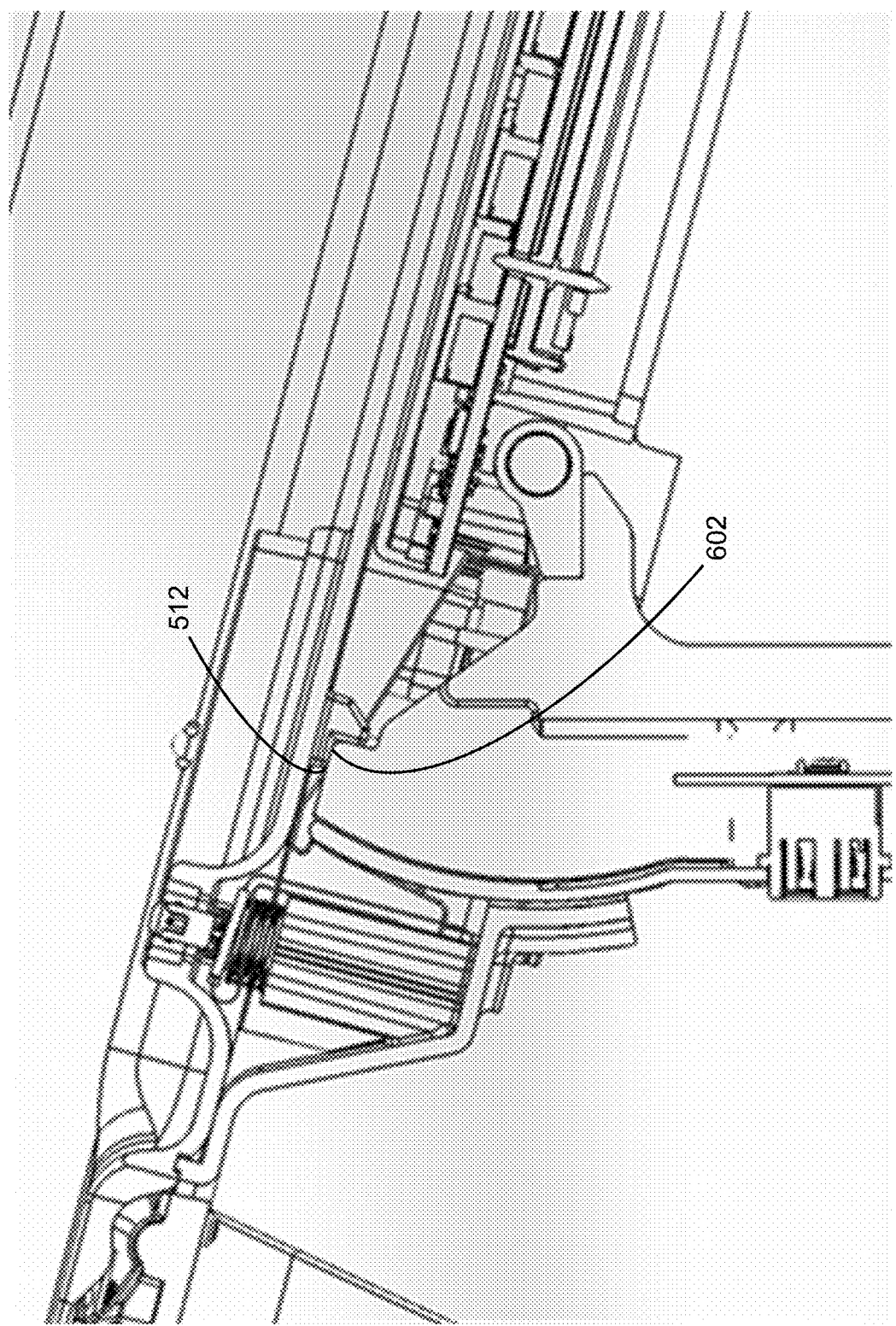
FIG. 6 is a cross sectional view of the tilt mechanism at an upper limit of motion in accordance with an embodiment of the present technology.

FIG. 6 is a cross sectional view of the tilt mechanism 406 at an upper limit of motion in accordance with an embodiment of the present technology. At the upper limit of motion, in one embodiment, the upper tilt stop 512 on the tilt mechanism 406 directly contacts an upper tab 602 (e.g., a bottom surface/portion that corresponds to/aligns with the upper tilt stop 512) of the docking tray 168. When the user pulls the handle 170 upward, thereby rotating the docking tray 168 upward (e.g., counter-clockwise direction as illustrated in FIG. 6), the upper tilt stop 512 provides a limit to the motion. In one embodiment, the upper tilt stop 512 is configured (e.g., a size, a location, etc.) to contact the upper tab 602 and provide an upper-limit, such as parallel to the horizontal plane or 15 degrees below the horizontal plane, in the range of motion for the docking tray 168 and/or the second interface 124.

Figure 7:
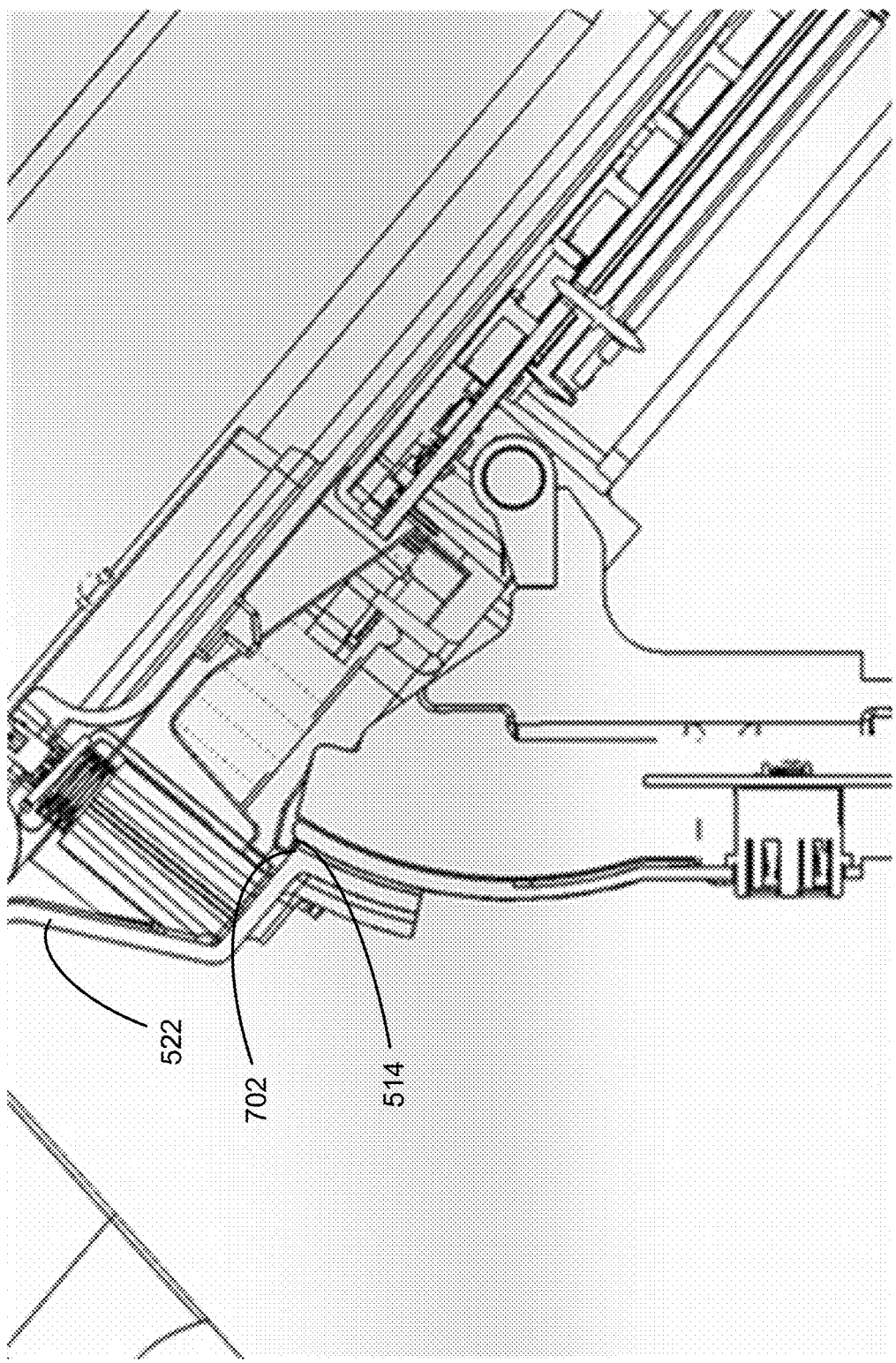
FIG. 7 is a cross sectional view of the tilt mechanism at a lower limit of motion in accordance with an embodiment of the present technology.

FIG. 7 is a cross sectional view of the tilt mechanism 406 at a lower limit of motion in accordance with an embodiment of the present technology. At the lower limit of motion, in one embodiment, the lower tilt stop 514 on the tilt mechanism 406 directly contacts a lower tab 702 (e.g., a top surface at a bottom portion that correspond to/align with the lower tilt stop 514) of the first hinge cover 522. When the user pulls the handle 170 downward, thereby rotating the docking tray 168 downward (e.g., clockwise direction as illustrated in FIG. 5), the lower tilt stop 514 provides a limit to the motion. In one embodiment, the lower tilt stop 514 is configured (e.g., a size, a location, etc.) to contact the lower tab 702 and provide a lower-limit, such as an angle between −55 to −90 degrees from horizontal, in the range of motion for the docking tray 168 and/or the second interface 124.

Figure 8:
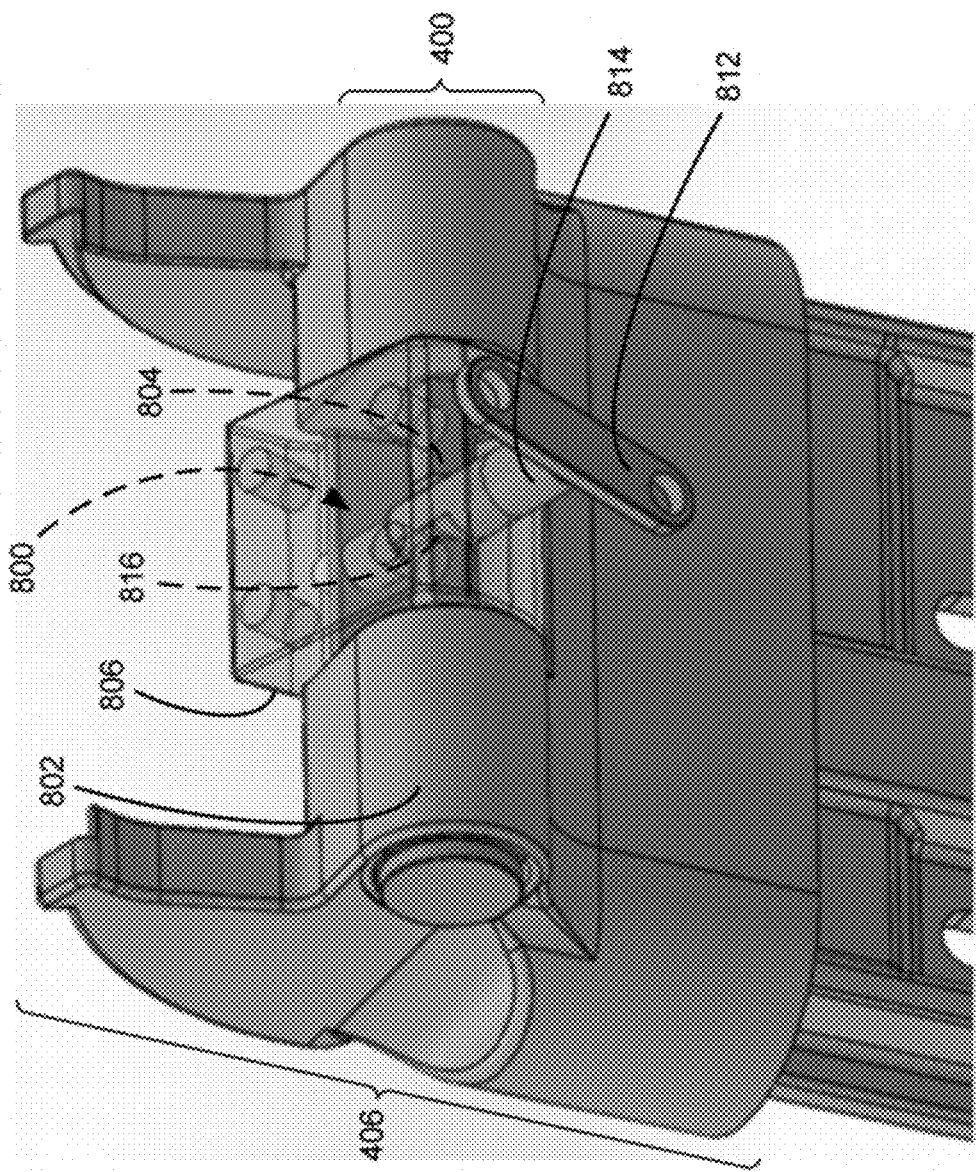
FIG. 8 is an isometric view of the tilt mechanism in accordance with an embodiment of the present technology.

FIG. 8 is an isometric view of the tilt mechanism 406 in accordance with an embodiment of the present technology. In some embodiments, the ultrasound imaging system 100 of FIG. 1 includes a barrel-type hinge for the adjustable hinge 400. For the barrel-type hinge, in one embodiment, the adjustable hinge 400 includes a barrel portion 802 surrounding/enclosing a pivot sleeve 804. Adjacent to or between the barrel portion 802, in one embodiment, the ultrasound imaging system 100 includes a docking tray interface 806 (e.g., an integral or a connected portion of the docking tray 168 of FIG. 1) surrounding/enclosing the pivot sleeve 804.

In one embodiment, the barrel portion 802 is attached to and is integral with the tilt mechanism 406. In one embodiment, the barrel portion 802 includes a hollow cylinder section where the rotational bearing force is applied to the pivot sleeve 804. In one embodiment, the pivot sleeve 804 (e.g., the pivot pin 502) is a sleeve (or a pin/rod in some embodiments) with a polygonal or a circular cross-sectional shape that extends parallel to a length of the barrel portion 802 and is enclosed within the barrel portion 802, and is configured to rotate within and relative to the barrel portion 802.

Similar to the barrel portion 802, in one embodiment, the docking tray interface 806 includes a clamp that fits over the pivot sleeve 804 and is secured thereto. When the docking tray 168 rotates, the pivot sleeve 804 can rotate with the docking tray interface 806 and within the barrel portion 802.

In some embodiments, the hinge includes an adjustable clutch mechanism 800 configured to provide different levels/amounts of resistance to rotation/movement of the docking tray interface 806. The adjustable clutch mechanism 800 includes a controller (not shown) operably coupled/connected to a clutch control 812 and a control arm 814 that together engage or disengage the clutch mechanism. For example, the controller can be a button, a lever, a dial etc. that the user can use to control the amount of resistance. In one embodiment, operation/displacement of the controller rotates the clutch control 812 and/or the control arm 814. In one embodiment, the adjustable clutch mechanism 800 is configured to convert the rotation of the clutch control 812 to a linear movement/force to adjust position or compression forces applied to one or more structures (e.g., plates, discs, etc., not shown) in the barrel portion 802 to change the amount of resistance relative to the rotation of the pivot sleeve 804 and the barrel portion 803. In one embodiment, the position is converted into data for the system by sensors as described herein, embedded within the ultrasound system, docking tray, the hinge, etc.

For the design illustrated in FIG. 8, in one embodiment, the control arm 814 is a cylinder/rod attached to, and integral with, the clutch control 812 and extends orthogonal to the control arm 814 and/or the pivot sleeve 804. The controller is connected to one or more ends of the clutch control 812, such that the clutch control 812 and the attached control arm 814 are rotated based on operation of the controller. In one embodiment, the control arm 814 includes a variable diameter engagement mechanism 816, such as a pair of depressions on the cylindrical surface, linearly aligned with a clutch pin that slides through the pivot sleeve 804. The position of the clutch pin determines how much force is required to move the hinge.

Figure 9:
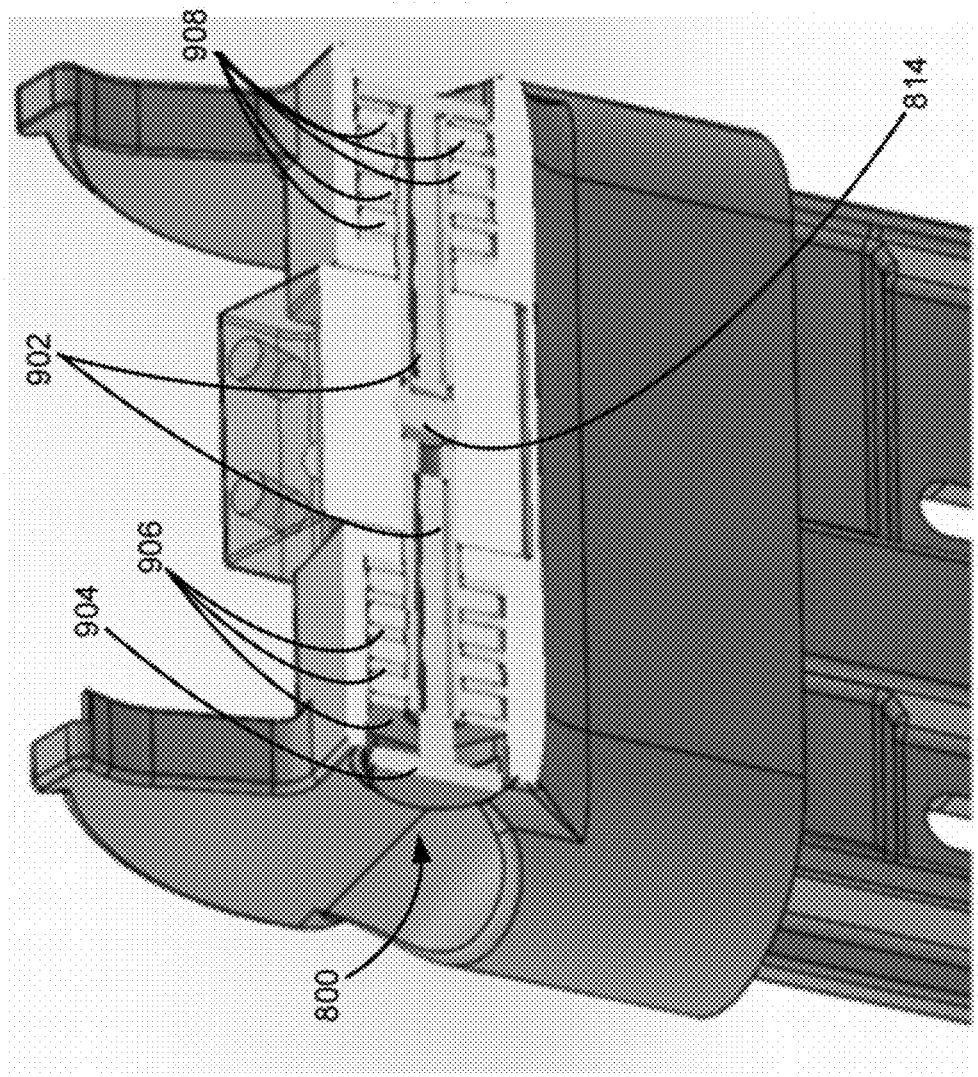
FIG. 9 is a partial cut-away view of the stand-head portion in accordance with an embodiment of the present technology.
Figure 10:
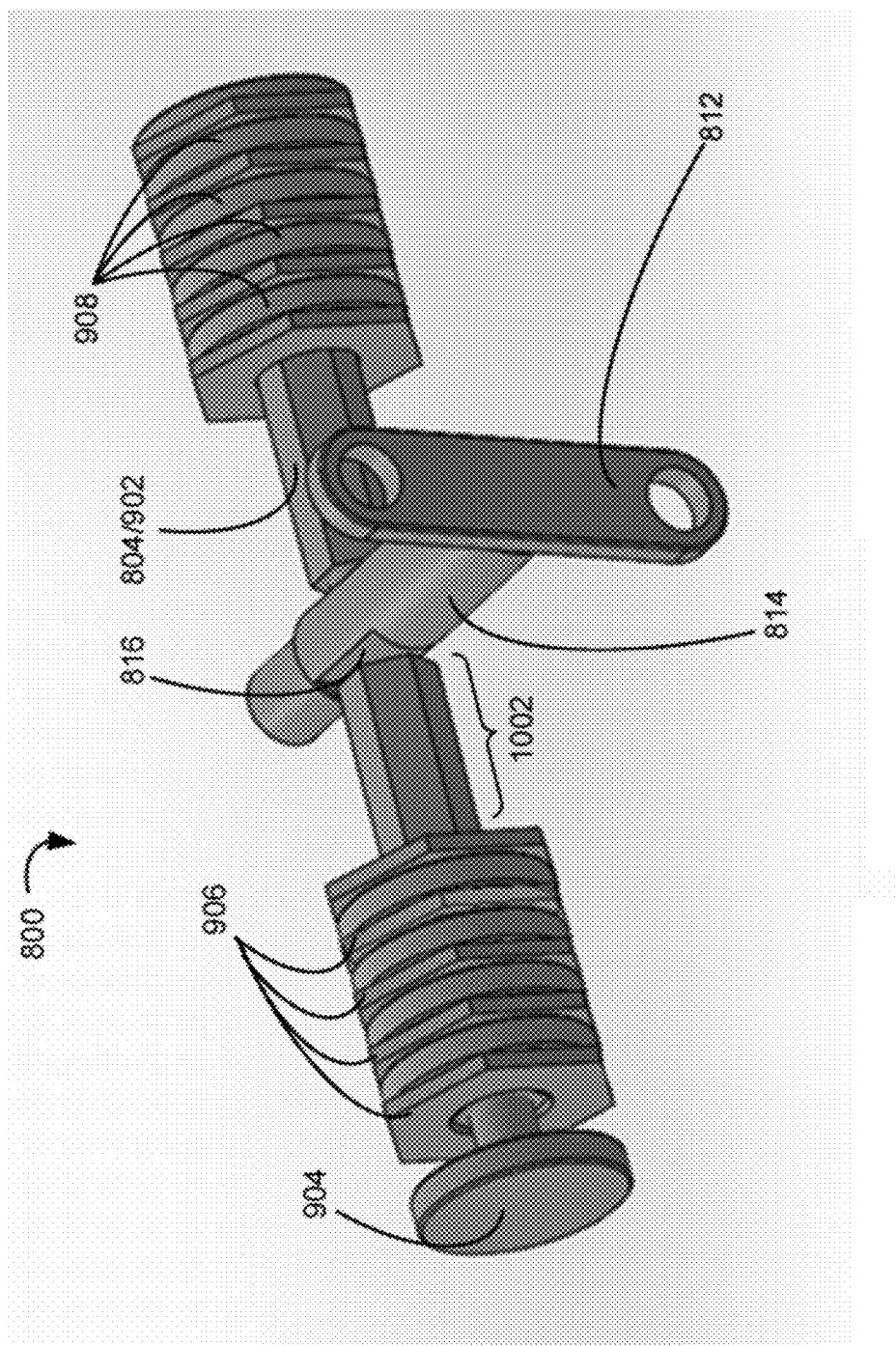
FIG. 10 is an isometric view of a clutch assembly in the barrel hinge in accordance with an embodiment of the present technology.

FIG. 9 is a partial cut-away view of the tilt mechanism 406 in accordance with an embodiment of the present technology. FIG. 10 is an isometric view of a clutch assembly in the barrel hinge in accordance with an embodiment of the present technology. FIG. 10 illustrates details of the example clutch mechanism 800. In one embodiment, the adjustable clutch mechanism 800 includes clutch pins 902 that are biased inward with a spring (not shown) positioned on the outside of a head 904 of the clutch pin. In one embodiment, locking plates 906 and washers 908 work together to adjust the amount of force required to move the pivot sleeve in the barrel hinge. The locking plates 906 have an outside shape (e.g., a hexagon) that cooperates with the inside shape of the hinge barrel, such that they do not rotate inside the hinge (e.g., remaining fixed relative to the barrel portion), and an inside hole that allows the pivot sleeve to rotate in the locking plates 906. The washers 908 are secured to the pivot sleeve by virtue of a cooperating shape (e.g., a hexagon) so that they rotate in the hinge as the pivot sleeve rotates. In one embodiment, both the locking plates 906 and the washers 908 are able to move slightly along the length of the pivot sleeve so they can be compressed together or released. In one embodiment, the head 904 of the clutch pin is forced by a spring secured to the inside end of the hinge against the locking plates/washers to increase the friction of the hinge. When the clutch pin 902 is forced outwardly by the camming action of the depression 816 in the control arm 814, the spring is compressed and the pressure at the locking plates 906 against the washers 908 is reduced, thereby allowing the pivot sleeve 804 of the hinge to move more easily in the barrel.

In some embodiments, the adjustable clutch mechanism 800 is configured to provide lower resistance to upward movement at the handle 170, thereby requiring lower amount of torque (e.g., half), than downward movement at the handle 170. In one embodiment, the adjustable clutch mechanism 800 is configured to provide resistance corresponding to force/torque amounts that comply with IEC 60601. For example, in one embodiment, the adjustable clutch mechanism 800 is configured (e.g., based on controlling surface friction between the plates and the washers, such as through material, surface shape or texture, etc.) to require about 10 pounds of pressure (e.g., a first resistance level) at the handle 170 to tilt/rotate the docking tray 168 upwards and about 20 pounds of pressure (e.g., a second resistance level) at the handle 170 to tilt/rotate the docking tray 168 downwards. In some embodiments, the locking plates 906 and/or the washers 908 includes a surface texture or shape that provides asymmetric levels of resistance based on the direction of force or relative movements.

In some embodiments, the adjustable clutch mechanism 800 is configured to disengage for upward movements and engage for downward movements via an unlock button or other control that moves the control arm 814 to relieve pressure on the plates and washers of the hinge. In some embodiments, the adjustable clutch mechanism 800 (e.g., the clutch control 812) is configured to engage and disengage the clutch directly based on initial movement or a direction of force applied at the handle 170. In one embodiment, the adjustable clutch mechanism 800 is configured to react to the initial movement or the direction of force without any separate controller.

In some embodiments, the adjustable clutch mechanism 800 is configured to provide some positive resistance when the clutch is disengaged (i.e., corresponding to a lower threshold amount of friction between the moving members, such as by relieving pressure from the outer springs). Accordingly, the adjustable clutch mechanism 800 can prevent the user from having to experience/support the maximum resistance of the imaging unit and the docking tray 168. In some embodiments, the adjustable clutch mechanism 800 is configured to provide an upper limit on resistance (e.g., based on strength/size/configuration of the springs) when the clutch is engaged. Accordingly, the adjustable clutch mechanism 800 can prevent the ultrasound imaging system 100 from tipping over (e.g., such as due to an excessive amount of force/leverage on the column 164 and the base portion 162) when the user manipulates the docking tray 168.

In some embodiments, the hinge mechanism 400 includes electrical connections/circuits. For example, in one embodiment, the within the hinge mechanism 400 includes a position sensing circuit, such as for angular/rotational positions of the docking tray 168. In one embodiment, the position sensing circuit is configured to detect an angle between the locking plates 906 and the pins 902. In one embodiment, the position sensing circuit is also configured to detect a position of the control arm 814 and/or the clutch control 812. Also for example, in one embodiment, the within the hinge mechanism 400 sends a signal to a processor of the ultrasound imaging system to transition between operating modes (e.g., a diagnostics mode and a procedural mode, such as corresponding to a first operating configuration or the second operating configuration). Also for example, in one embodiment, the adjustable clutch mechanism 800 includes a grounding circuit or a shielding circuit (e.g., an electro-magnetic interference (EMI) shield). The areas of contact for the shielding circuit can be increased through the locking plates 706 and/or the washers 708, thereby providing an increase in EMI shielding capacity.

Figure 11:
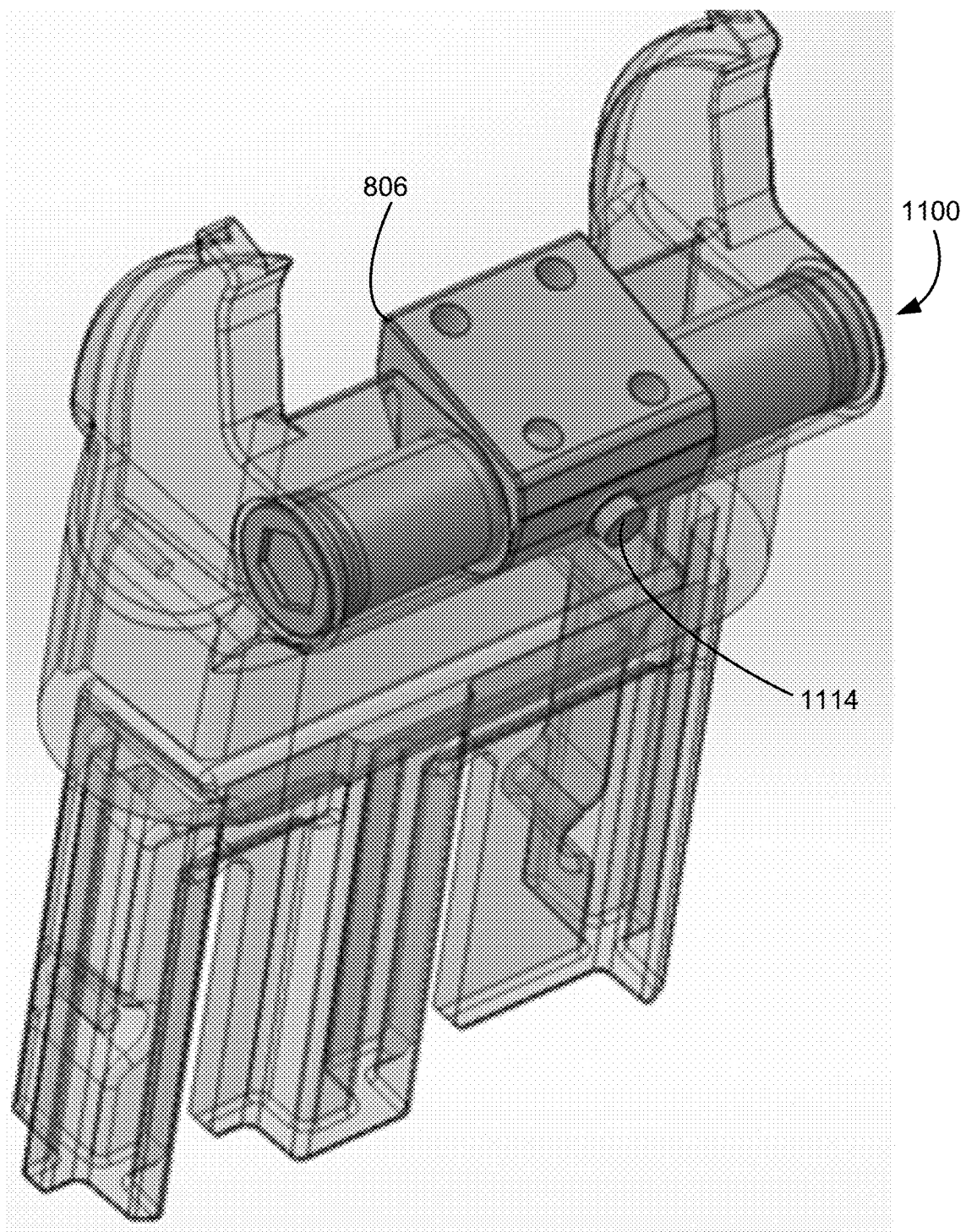
FIG. 11 is an internal view of the tilt mechanism with an upper portion of the stand-head in accordance with a further embodiment of the present technology.
Figure 12:
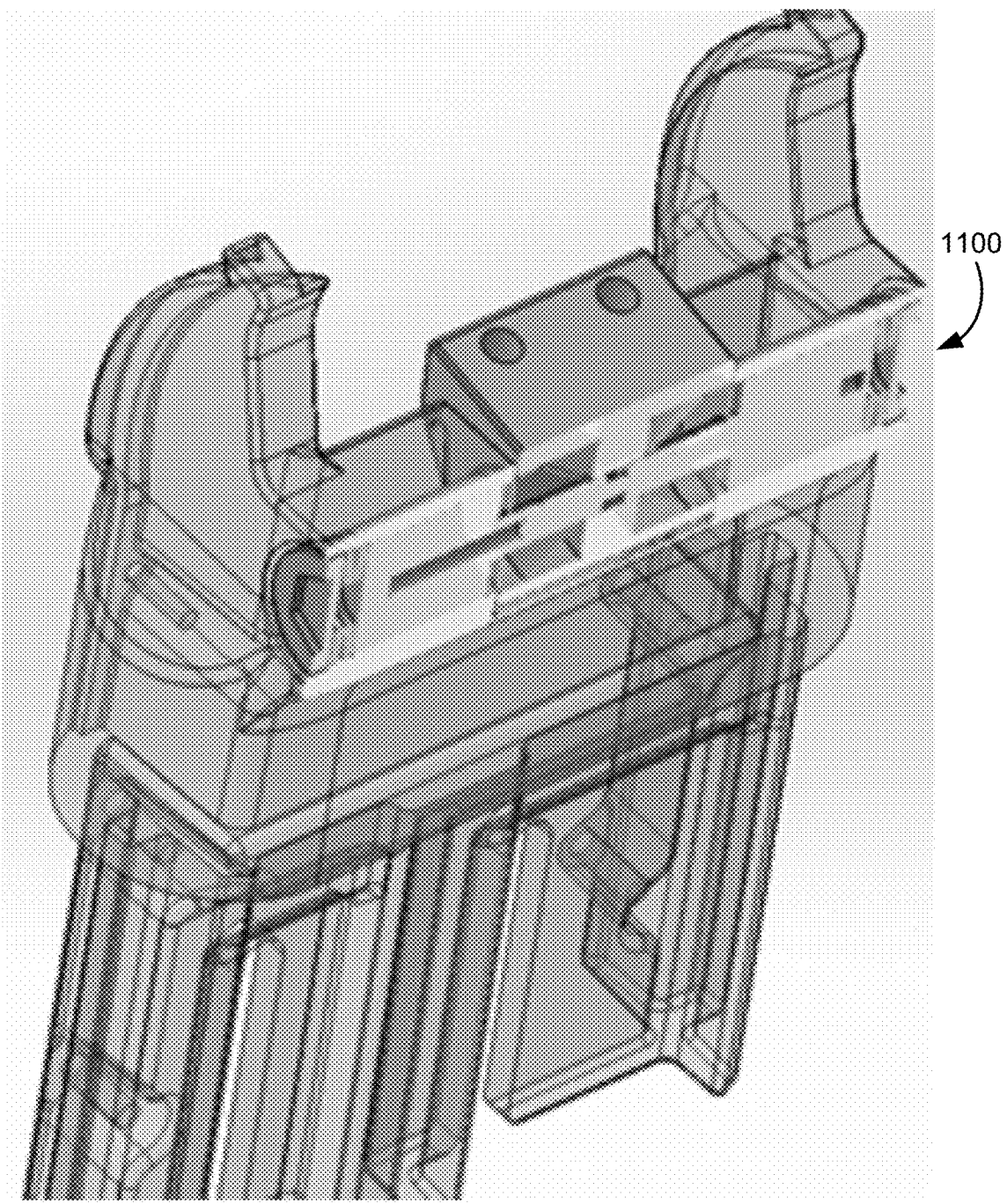
FIG. 12 is a partial cut-away view of the tilt mechanism in accordance with an embodiment of the present technology.

FIGS. 11-12 illustrate an example clutch mechanism 1100 within the tilt mechanism 406. FIG. 11 is an internal view of the tilt mechanism 206 in accordance with a further embodiment of the present technology. FIG. 12 is a partial cut-away view of the tilt mechanism 206 in accordance with an embodiment of the present technology. In some embodiments, the ultrasound imaging system 100 of FIG. 1 includes the clutch mechanism 1100 corresponding to a linear-to-axial design. For example, the clutch mechanism 1100 includes a spring loaded control arm 1114 that is pushed in/out by an engagement mechanism (not shown). In one embodiment, the linear inward/outward movement of the control arm 1114 is converted into an axial force/movement (e.g., such as by ramping cuts in the diameter of the control arm 1114) that engages/disengages the structures (e.g., plates, washers, etc.) located inside a barrel portion 1102.

In some embodiments, a clutch mechanism is a wrap-spring design (not shown). For example, in one embodiment, the clutch mechanism includes a spring wrapped around a turning rod (e.g., the hinge pins). The spring winding can provide asymmetric resistance to opposing directions of rotation/movement of the turning rod. Further, the spring can be operably connected to a clutch control, a control arm, etc. that are configured to push against one or more end portions of the spring, thereby partially unwinding the spring and releasing tension. Accordingly, the user can operate the clutch control, the control arm, etc. to unwind the spring or a portion thereof and decrease the resistance (e.g., to the rotation/movement of the hinge pin) provided by the spring.

In one embodiment, the adjustable hinge 400 includes the clutch mechanism 600/800/900 that provides differing/asymmetric resistances to opposing directions of rotation/movement. Accordingly, the adjustable hinge 400 with the clutch mechanism provides user-selectable state of torque (e.g., higher torque when the clutch is un-actuated, and lower torque during actuation, to allow the user to reposition the imaging system at different orientations.

In some embodiments, the tilt mechanism 206 includes cavities configured to hold or house wires/cables therein. In one embodiment, the adjustable hinge 400 with the clutch mechanism 600/800/900 is configured to route electrical signals to/from the wires/cables in the cavities. Accordingly, at least a portion of the electrical wiring for the ultrasound imaging system 100 can be made internally within/through the docking tray 168, the adjustable hinge 200, the column 164, etc.

Figure 13:
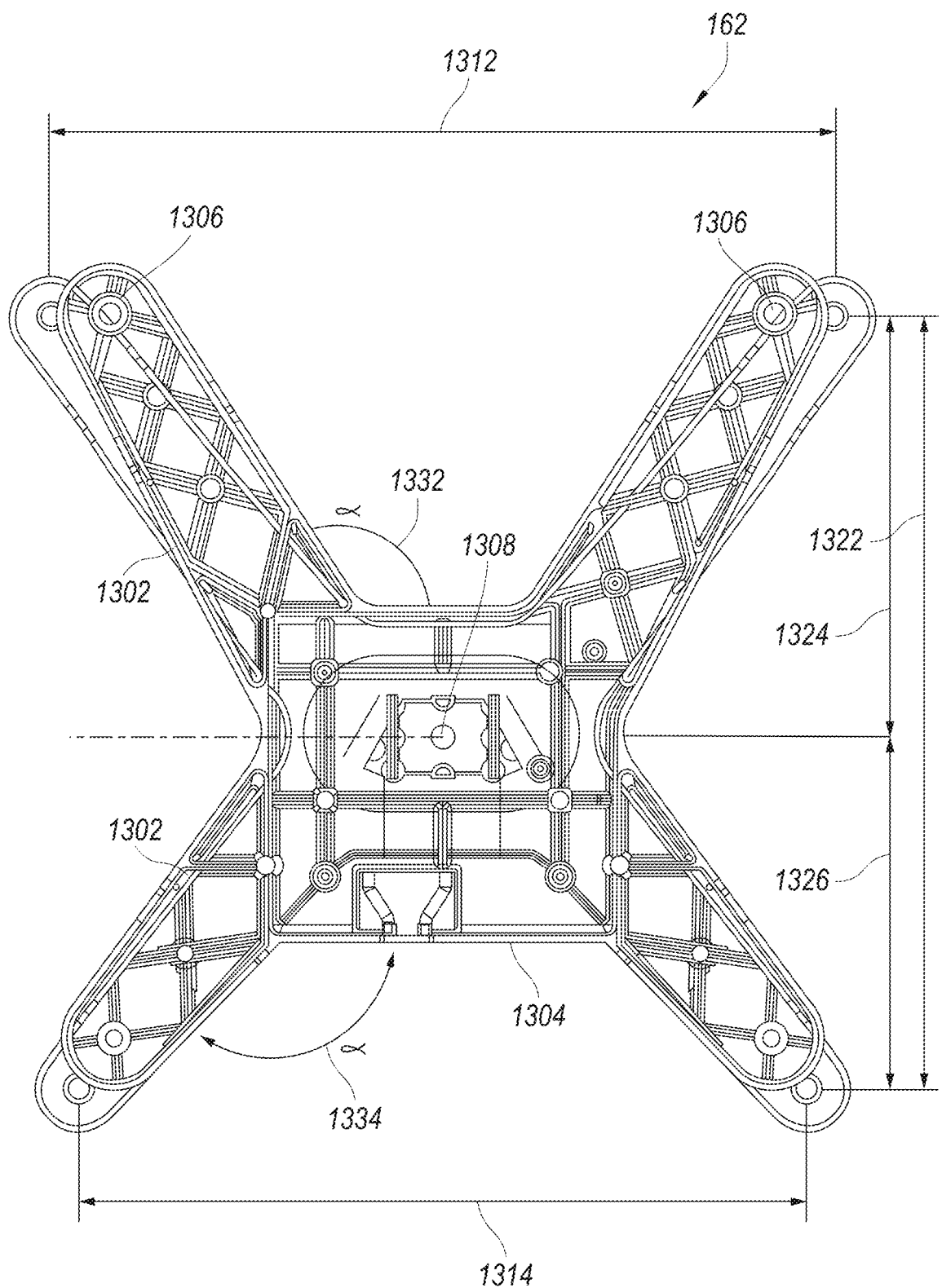
FIG. 13 is a plan view of a base of a stand in accordance with an embodiment of the present technology.

FIG. 13 is a plan view of a base (e.g., the base 162) of a stand (the stand 150 of FIG. 1) in accordance with an embodiment of the present technology. In some embodiments, the base 162 includes four legs 1302 extending from a core portion 1304. In one embodiment, two legs 1302 extend forward (i.e., toward a medical operator facing and operating the imaging device) and two legs 1302 extend backward (i.e., away from a medical operator) from the core portion 1304. The legs 1302 extend horizontally away from each other, away from a center line, etc. In other words, each of the legs 1302 form an angle (e.g., a first angle 1332 ($\alpha_1$), a second angle 1334 ($\alpha_2$), etc.) greater than 90° in reference to a corresponding edge of the core portion 1304. FIG. 13 shows two example designs for the base 162, wherein one design (e.g., shown on the outside) includes longer legs that are wider apart.

At distal ends (e.g., opposite the core portion 1304), each of the legs 1302 include a wheel receiver 1306 configured to connect to wheels (e.g., caster pins). In some embodiments, the wheel receivers in the front are spaced apart by a front separation width 1312 ranging between 15-25 inches. In one embodiment, the wheel receivers in the back are spaced apart by a back separation width 1314 ranging between 14-24 inches, while the wheel receivers in the front and the back are spaced apart by a separation length 1322 ranging between 15-25 inches. Relative to a column-attachment portion 1308 (e.g., a location on the core portion 1304) configured to attach to the column 164 of FIG. 1, such as a center portion of the core portion 1304), the front wheels can extend forward by a front length 1324 (e.g., ranging between 5-15 inches) along a front direction. In one embodiment, he back wheels extend backward from the column-attachment portion 1308 by a back length 1326 (e.g., ranging between 5-15 inches).

In some embodiments, the legs are symmetrical (e.g., in size and orientation) to the center line. In some embodiments, the front separation width 1312 can be longer than the back separation width 1314. For example, in one embodiment, the front separation width 1312 can be about 20 inches and the back separation width 1314 can be about 19 inches. In some embodiments, the front length 1324 is longer than the back length 1326. For example, in one embodiment, the front length 1324 is about 11 inches and the back length 1326 can be about 9 inches. In some embodiments, the first angle 1332 is the same as the second angle 1334. For example, in one embodiment, the first angle and the second angle can be around 130 degrees. In other embodiments, the first angle 1332 is smaller than the second angle 1334. Based on the larger angle, the shorter back legs can horizontally (e.g., perpendicular to the front-back direction) extend a similar distance from the core portion 1304 as the longer front legs.

Based on the shape and configuration of the column 164 of FIG. 1 and the tilt mechanism 406, the handle 170 of FIG. 1, and the adjustable hinge 400 of FIG. 4, a center of gravity for the imaging unit and the docking tray 168 of FIG. 1 is positioned in front of the column-attachment portion 1308. Together with the base 162, the above configuration provides reduced space requirement/system footprint. The longer front legs (i.e., relative to the column-attachment portion 1308) can prevent the system from tipping forward when the user pushes down on the handle 170. The column 164 located behind the adjustable hinge 400 and the center of gravity point prevents the system from tipping backward when the user pulls up on the handle 170, even with the shorter back legs. In one embodiment, the overall system size/foot print can be further reduced based on the adjustable hinge 400 providing differing/asymmetric resistances. The coaxial arrangement of the clutch and the hinge axes can reduce the space necessary to implement the hinge and the clutch mechanism.

Figure 14B:
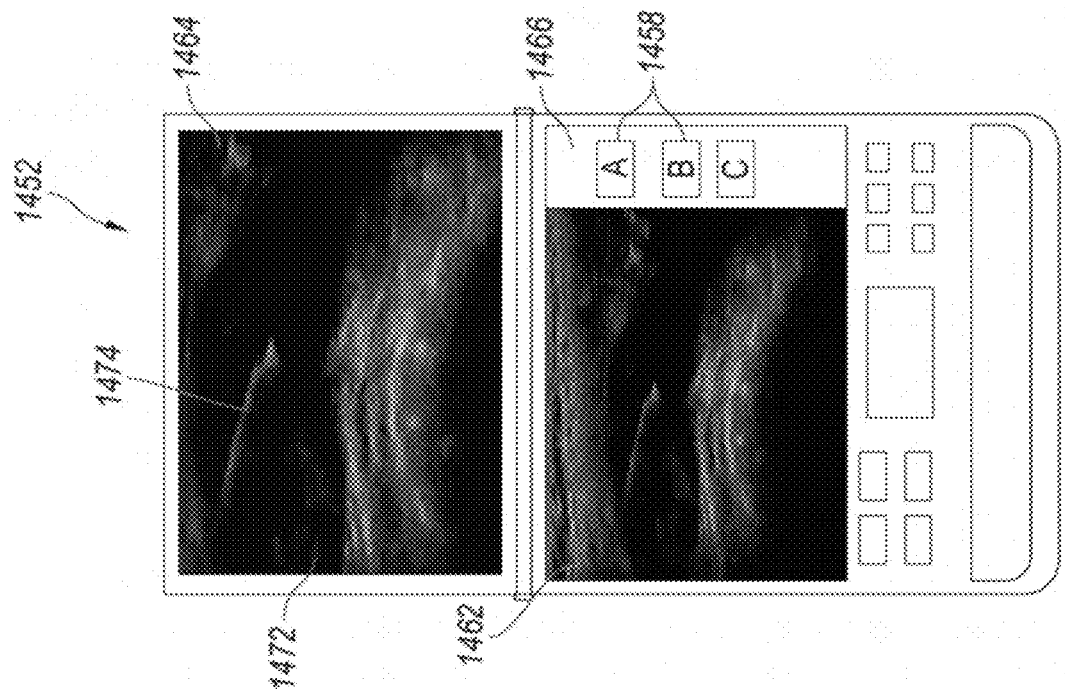
FIG. 14B illustrates example displays for a procedural mode in accordance with an embodiment of the present technology.
Figure 14A:
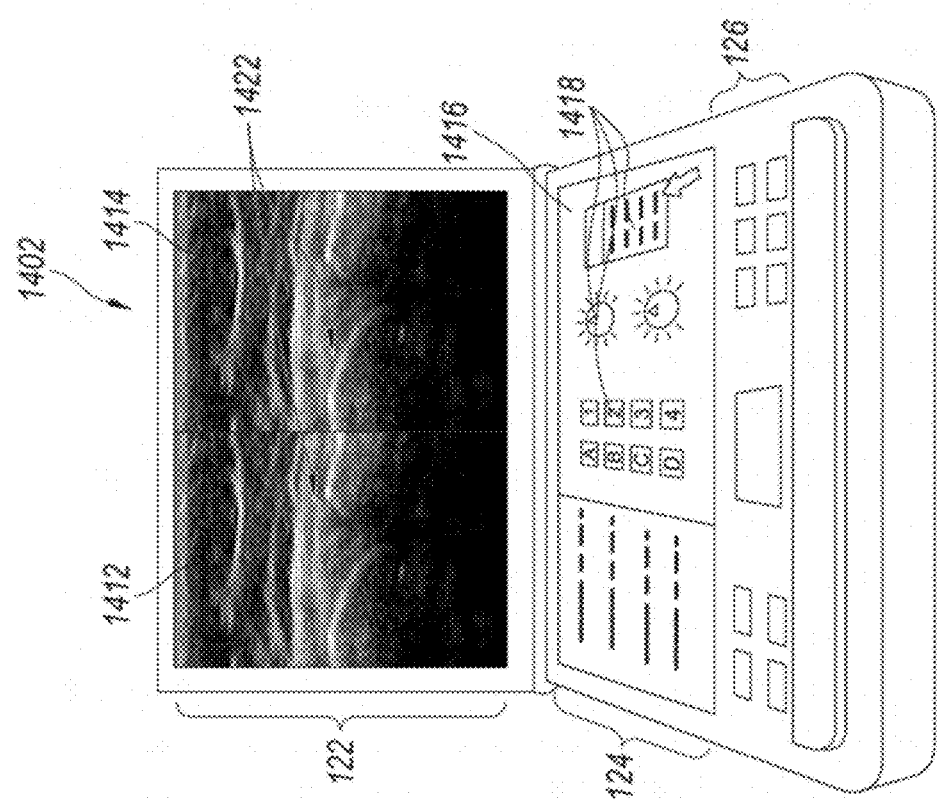
FIG. 14A illustrates example displays for a diagnostic mode in accordance with an embodiment of the present technology.

FIGS. 14A and 14B illustrate example displays for different operating modes in accordance with an embodiment of the present technology. For example, FIG. 14A illustrates a front view of the imaging device of FIG. 1B in the first operating configuration 202 of FIG. 2. Accordingly, FIG. 14A illustrates example displays of the imaging device (e.g., the first interface 122, the second interface 124, etc., all of FIG. 1B) configured according to a diagnostics mode 1402. Also, FIG. 14B illustrates a front view of the imaging device in the second operating configuration 204 of FIG. 2. Accordingly, FIG. 14B illustrates example displays configured according to a procedural mode 1452.

As discussed above, in one embodiment, an operator changes/sets the orientation of the ultrasound imaging system 100 (e.g., the base portion 114 of FIG. 1, the second interface 124, the docking tray 168 of FIG. 1, etc.). For example, in one embodiment, the operator uses the handle 170 to rotate the docking tray 168 about the adjustable hinge 402 of FIG. 4.

In one embodiment, the ultrasound imaging system 100 detects the orientation (e.g., the first operating configuration 202 or the second operating configuration 204) of the docking tray 168 and/or the second interface 124. The ultrasound imaging system 100 can select the operating configurations (e.g., the first operating configuration 202 or the second operating configuration 204) using various mechanisms. For example, in one embodiment, the ultrasound imaging system 100 (e.g., the imaging device, the docking tray 168, the adjustable hinge 402, etc.) includes an accelerometer, a gyroscope, a position encoder, a switch, etc. configured to detect the orientation of the imaging device (e.g., the second interface) or a change thereof. Also for example, in one embodiment, the ultrasound imaging system 100 includes a sensor or a circuit or connect to an external censor or circuit configured to determine a height of the mounting portion or a length of the vertical portion. In one embodiment, the ultrasound imaging system 100 uses the detected orientation and/or the detected height to initiate/implement either the diagnostic mode or the procedural mode.

In one embodiment, detection of the first operating configuration 202 triggers implementation of the diagnostics mode 1402, and detection of the second operating configuration 204 triggers implementation of the procedural mode 1454. The ultrasound imaging system 100 implements the different modes by adjusting probe or ultrasound signal settings (e.g., the gain, the focal zone, the signal frequency, etc.), controlling display settings (e.g., location/size/color of the visual depiction, the graphic user interface, settings/status, etc.), adjusting input/control sensitivity (e.g., touch/pressure sensitivity, change rate/magnitude, etc.), etc.

In one embodiment, in the diagnostics mode 1402, the ultrasound signal settings are selected to detect human tissue without accounting for inorganic material. For the procedural mode 1452, the ultrasound signal settings are selected to detect inorganic material, such as needles, cutting tools, probes, stents, catheters etc. Also for example, in one embodiment, the ultrasound imaging system 100 provides a full set of controls and/or granularity for the diagnostics mode 1402 and a limited/selected set of controls and/or granularity for the procedural mode 1452. Since an operator is typically seated in front of the ultrasound imaging system 100 with one hand available to access the interface(s) on the ultrasound imaging system 100 (e.g., the first interface 122, the second interface 124, and/or the tactile interface portion 126) of the ultrasound imaging system 100 during most diagnostic exams, the ultrasound imaging system 100 can provide a greater set of controls. In contrast, the medical professional performing a medical procedure is often further away from the ultrasound imaging system 100 and/or with the patient located between the medical professional and the interfaces. Further, during the medical procedures, both hands of the medical professionals are often occupied, with one holding the procedural equipment and the second hand holding the ultrasound probe. As such, in one embodiment, the ultrasound imaging system 100 highlights or enhances buttons or GUI portions (e.g., a predetermined set of buttons or GUIs, a set of buttons or GUIs that have been accessed most or over a predetermined number of times within a given duration, etc.) that are necessary or correspond to often-accessed features and/or reduce or eliminate less-accessed features.

In some embodiments, as illustrated in FIG. 14A, the imaging device displays a first diagnostics image 1412 and/or a second diagnostics image 1414 for the diagnostics mode 1402. The first diagnostics image 1412 and the second diagnostics image 1414 can show visualization of tissue 1422 in the scanned region. In some embodiments, the first diagnostics image 1412 and the second diagnostics image 1414 highlight different aspects of the scanned tissue 1422. For example, in one embodiment, the first diagnostics image 1412 is a color image or a 3-D image and the second diagnostics image 1414 is a black-and-white image or a 2-D image. In some embodiments, the first diagnostics image 1412 and/or the second diagnostics image 1414 are displayed on the first interface 122.

In some embodiments, the second interface 124 (e.g., a touch screen) displays a diagnostics graphic user interface (GUI) 1416 for the diagnostics mode 1402. The diagnostics GUI 1416 is configured to communicate settings, controls, etc. with the operator. In one embodiment, the GUI 1416 includes graphic control items 1418 (e.g., a full set of controls) configured to receive user inputs/controls for operating the ultrasound imaging system 100. For example, the graphic control items 1418 (e.g., buttons, dials, drop-down menus, etc.) can be configured to adjust probe settings (e.g., imaging mode, B-mode, Doppler, color flow, the gain, the focal zone, the signal frequency) and/or display settings (e.g., location/size/color/contrast/brightness of the visual depiction).

For the procedural mode 1452, in one embodiment, the ultrasound imaging system 100 accounts for the operator being further away from the system, having the patient between the system and the operator, the operator having both hands occupied (e.g., with a probe and a medical instrument), etc. In the procedural mode 1452, in one embodiment, the ultrasound imaging system 100 dedicates more of the screen space to display the scanned results and/or reduce or simplify the GUI controls.

As illustrated in FIG. 14B, in one embodiment, the imaging device displays a first procedural image 1462 and/or a second procedural image 1464 for the procedural mode 1452. In some embodiments, the first procedural image 1462 and/or the second procedural image 1464 can be larger than the first diagnostics image 1412 and/or the second diagnostics image 1414. For example, in one embodiment, the first procedural image 1462 fills the first interface 122 and the second procedural image 1464 fills the second interface 124 instead of the first diagnostics image 1412 and the second diagnostics image 1414 sharing a screen. In some embodiments, the ultrasound imaging system 100 displays one image for the diagnostics mode 1402, and simultaneously display both the first procedural image 1462 and the second procedural image 1464 in the procedural mode 1452. For example, in one embodiment, the first procedural image 1462 and the second procedural image 1464 show images having different zoom levels, images resulting from different processing/filtering, images from different feeds/sources, etc. In some embodiments, the ultrasound imaging system 100 displays one image continuously across both the first interface 122 and the second interface 124.

The ultrasound imaging system 100 further presents a procedural GUI 1466 including simplified control items 1458 (e.g., a reduced set of the graphic control items 1418). The ultrasound imaging system 100 displays the procedural GUI 1466 including a predetermined set (e.g., predetermined by the system manufacturer, the operator, or a combination thereof) of controls that is less than the diagnostics GUI 1416. In some embodiments, the simplified control items 1458 have larger display/input size, larger separation between items, etc. In some embodiments, the second interface 124 displays soft controls (e.g., GUI items) without any ultrasound images during the diagnostics mode and displays one or more ultrasound images or a portion thereof during the procedural mode.

In some embodiments, the ultrasound imaging system 100 is configured to use additional information to further update the settings. For example, in one embodiment, the ultrasound imaging system 100 receives or determines the additional information, such as operator identification, patient identification, patient medical profile/history, system location (e.g., identity of the examination room), appointment/scheduling calendar, etc. In one embodiment, the ultrasound imaging system 100 receives or determines the additional information based on receiving log-on information or operator-provided information, calculating the device location (e.g., geofence-based detection, WIFI-based calculation, etc.), receiving patient information and/or scheduling information from another device (e.g., hospital mainframe), etc. Using the additional information, in one embodiment, the ultrasound imaging system 100 identifies a specific exam or procedure being conducted and adjust the settings accordingly. For example, in one embodiment, the ultrasound imaging system 100 identifies a specific region and/or depth of the patient's body targeted by the procedure/exam based on the additional information, and adjusts the ultrasound signal settings, the display settings, the control settings, etc. accordingly. The ultrasound imaging system 100 can implement the settings for the specific exam/procedure based on detecting an orientation of the ultrasound imaging system 100.

Figure 15:
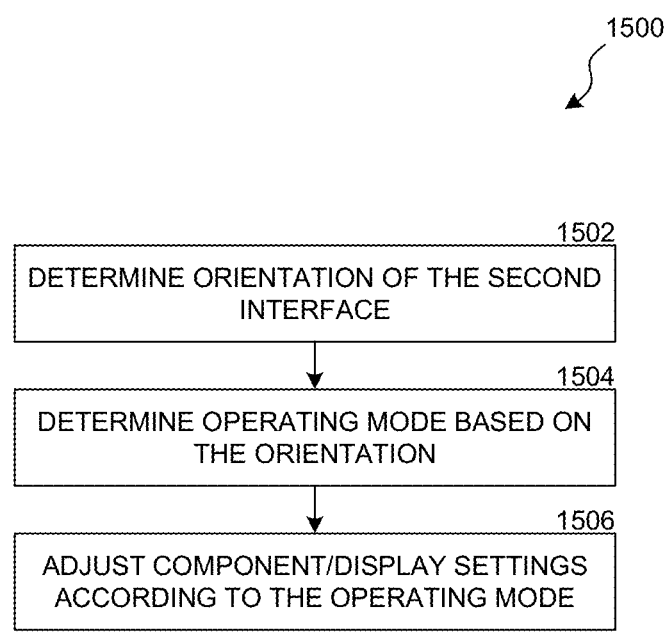
FIG. 15 is a flow diagram of a method or process of adjusting operational settings according to a detected orientation of the imaging system in accordance with an embodiment of the present technology.

FIG. 15 is a flow diagram of a method or process 1500 of adjusting operational settings according to a detected position or orientation of the ultrasound imaging system 100 of FIG. 1A in accordance with an embodiment of the present technology. The method can be for operating an ultrasound imaging system (e.g., the ultrasound imaging system 100 of FIG. 1A).

At block 1502, a processor in the ultrasound imaging system 100 executes programmed instructions to determine an orientation of a portion therein (e.g., the lid 112 of FIG. 1A, the base portion 114 of FIG. 1A, the first interface 122 of FIG. 1B, the second interface 124 of FIG. 1B, the docking tray 168 of FIG. 1A, or a combination thereof). In some embodiments, the ultrasound imaging system 100 includes an accelerometer, a gyroscope, a position encoder, a camera, or a combination thereof configured to determine or estimate the orientation of the portion(s) of the ultrasound imaging system 100. In some embodiments, the ultrasound imaging system 100 (e.g., the adjustable stand) includes one or more switches, position detection circuits, etc. configured to determine the orientation of the second interface 124, the docking tray 168, or a combination thereof. In some embodiments, the determined orientation can be an angle between the second interface 124 and a horizontal plane and/or an angle between the first interface 122 and the second interface 124.

At block 1504, the processor of the ultrasound imaging system 100 determines an operating mode based on the determined orientation. In some embodiments, the processor selects the diagnostics mode 1402 of FIG. 14 or the procedural mode 1452 of FIG. 14 that corresponds to the determined orientation. For example, in one embodiment, the procedural mode 1452 and the diagnostics mode 1402 correspond to a range of angles. In some embodiments, the diagnostics mode 1402 corresponds a first threshold range that is nearest to being parallel to the horizontal plane, that includes 0° to −15°, or a combination thereof. In some embodiments, the procedural mode 1452 corresponds to a second threshold range that is nearest to a vertical plane, that includes −55°, or a combination thereof. The processor is programmed to select the operating mode based on comparing the determined angle to the threshold ranges. In some embodiments, portions of the first threshold range and the second threshold range can overlap, and the processor can use other additional factors (e.g., movement direction, previous mode, etc.) to determine the mode.

At block 1506, the processor adjusts one or more component settings, signal processing, and/or display settings according to the determined operating mode. For example, the processor selects a probe and/or a transducer, sets the signal characteristic (e.g., the gain, the focal zone, the frequency, etc.), sets or selects digital signal filter taps, displays/hides GUI, adjusts location/size of the GUI, changes image properties (e.g., brightness, color, size/zoom/focus, annotations, etc.), adjusts sensitivity of one or more buttons/controls on the tactile interface portion, disables/enables one or more buttons/controls on the tactile interface portion, etc. Accordingly, the processor can provide images and controls that correspond to the exam or the procedure being conducted with the ultrasound imaging system 100.

In some embodiments, the processor of the ultrasound imaging system 100 is programmed to display less detail, display a larger processed image, increase brightness and/or contrast, remove/restrict controls, etc. for the procedural mode in comparison to the examination mode. In some embodiments, for the procedural mode, one of the interfaces can display the real-time results of processing the ultrasound echo, and the other interface can simultaneously display workflow information, captured image, micro-image (e.g., a focused portion of the overall image), video demonstration or other reference images, etc.

In some embodiments, the method can further include storing real-time adjustments made during the exam/procedure. The processor can correlate the adjustments to the patient, the exam type, the operator, the system location, etc. When the corresponding operating mode is initiated for the same patient, same exam, same operator, same location, etc., the ultrasound imaging system 100 can recall and implement the previously saved/updated settings.

In some embodiments, the method can further include ending the implemented mode, automatically saving one or more images, initiating a worksheet application, etc. based on determining a change in the orientation. For example, when the operator brings up the second interface (e.g., from the larger angular orientation to the smaller angular orientation), the ultrasound imaging system 100 can automatically end the procedural mode, automatically save one or more images stored in a temporary buffer to a permanent record/storage (e.g., such as the before/needle position/after images for injection procedures), and/or automatically bring up an application corresponding to after-procedure/exam report (e.g., the worksheet).

Figure 16:
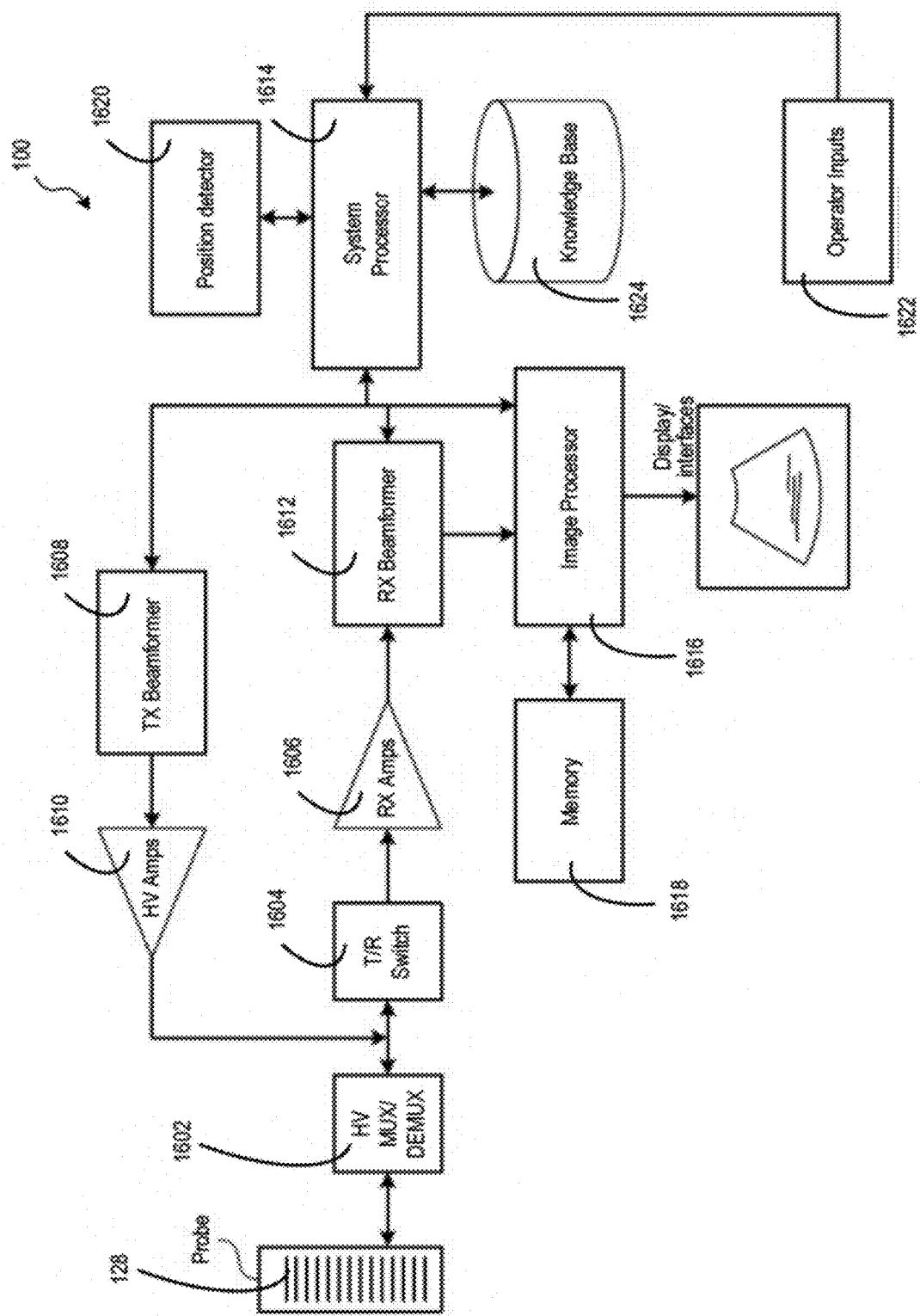
FIG. 16 is a block diagram of the ultrasound imaging system shown in FIG. 1A in accordance with an embodiment of the present technology.

FIG. 16 is a simplified block diagram of a system configured in accordance with an embodiment of the present technology. As will be appreciated by those skilled in the art, the ultrasound imaging system 100 may be constructed with components that are different than those shown in FIG. 15. In addition, the ultrasound imaging system 100 can include components that are not discussed (e.g., a power supply, etc.) and that are not necessary for the understanding of how to make and use the present technology.

In the illustrated embodiment, the transducer probe (e.g., the probe 128 of FIG. 1) is connected to a high voltage multiplexer/de-multiplexer (HV mux/demux) 1602 that is used select individual or groups of transducer elements in the transducer probe. In the case of a phased-array, signals to be transmitted by the transducer probe are generated by a transmit (TX) beamformer 1608 that adjusts the timing of the signals in order to direct acoustic signals in a particular direction and to focus the signals at a particular depth in the tissue. Alternatively, unfocused (plane) acoustic waves can be transmitted by the transducer probe. Signals from the TX beamformer 1608 are amplified by one or more high-voltage amplifiers (HV amps) 1610 before being applied to the HV mux/demux 1602 and the transducer probe.

A transmit/receive (T/R) switch 1604 operates to disconnect the receive electronics of the ultrasound imaging system 100 from the transducer probe when the higher powered transmit pulses are being transmitted. The T/R switch 1604 is closed when the ultrasound imaging system 100 is to detect the returning echo signals. Signals received by the T/R switch 1604 are amplified by low-noise receive amplifiers (RX amps) 1606 that implement a gain function that typically varies according to the depth from which the echo signals originate. Where the ultrasound imaging system 100 is a directional ultrasound system, the outputs of the RX amps feed a receive (RX) beamformer 1612 that delays and sums the amplified received echo signals. In some embodiments, the analog received signals are converted to corresponding digital signals, after amplification, with a number of analog to digital converters (not shown) that are positioned in the signal path between the RX amps 1606 and the RX beamformer 1612.

In some embodiments, a system processor 1614, which can be implemented as one or more programmed microprocessors (e.g., one or more central processing units (CPU), one or more graphics processor units (GPU), one or more digital signal processors (DSP), or combinations thereof), is configured to execute program instructions that are stored in an internal or external computer readable memory (not shown) to control the operation of the ultrasound imaging system 100. As further illustrated in FIG. 16, beamformed ultrasound signals produced by the RX beamformer 1612 are delivered to an image processor 1616. The image processor 1616, which may include one or more general purpose microprocessors (including the system processor 1614), one or more DSP, one or more GPU, application-specific integrated circuits (ASIC) or the like, converts the raw, beamformed signals into a two-dimensional image frame of pixel data that can be stored in memory and shown to the operator on the display.

The image frames produced by the image processor are stored in memory 1618. In one embodiment, the memory 1618 can store 2-5 minutes of data at 30 frames/sec or 3600-9000 image frames of ultrasound data or more. The memory 1618 can be used to store the image frames for archival purposes. The contents of the memory 1618 may be transferred to a remote patient records keeping system after an imaging procedure is complete.

In some embodiments, the ultrasound imaging system 100 includes a position detector 1620 configured to determine an orientation of one or more portions therein (e.g., the lid 112 and/or the base portion 114, an interface therein, the docking tray 168, etc.). For example, the position detector 1620 can include an accelerometer, a gyroscope, a push button, a position-detection circuit, an angle encoder, etc. The position detector 1620 can provide the orientation information to the system processor 1614. In some embodiments, the position detector 1620 can be included in the imaging unit. In some embodiments, the position detector 1620 can be included in the adjustable stand 150 (e.g., the docking tray 168, the adjustable hinge 402, etc.). Accordingly, the position detector 1620 can communicate the orientation information from the adjustable stand 150 to the imaging unit. In response to the detected position/orientation of the ultrasound imaging system 100, the system processor 1614 is configured/programmed to select the operating mode and implement the corresponding settings.

In the illustrated embodiment, the ultrasound imaging system 100 includes a number of operator inputs 1622 (e.g., the tactile interface portion 126) such as keys, buttons, knobs, a microphone to receive voice commands, a camera to capture gestures, or software-configured controls (e.g., GUI), such as touch screen controls or the like. The operator inputs 1622 allow an operator to change the operating characteristics of the ultrasound imaging system 100 and to input commands to the system processor 1614.

In some embodiments, the operator begins an ultrasound imaging procedure (e.g., an examination) by adjusting/selecting the position/orientation of the ultrasound imaging system 100. In some embodiments, in one embodiment, the operator further selects a procedure type from a number of pre-defined procedure types that are shown on the display or that may have a dedicated control on a keyboard or other input device of the ultrasound imaging system 100.

For example, the imaging procedure could be a regional anesthesia injection or other ultrasound-guided needle injection procedure. Each procedure type may be associated with particular settings (e.g., for transducer, signal, display, input/output, etc.) corresponding to views and/or measurements that are to be made by the operator during the specific exam/procedure. In the illustrated embodiment, the settings required by the various exam/procedure types can be stored in a knowledge base 1624 (e.g., a memory, database, etc.) that is accessible to the system processor 1614. In some embodiments, the knowledge base 1624 can include a set of user-specified settings or often-accessed settings (e.g., based on a recently accessed count, such as for a running window, for each features/buttons/GUIs) for one or a group of users, for the diagnostic/procedural mode, etc. The ultrasound imaging system 100 can implement the user-specified settings or the often-accessed settings when implementing or switching between the operating modes for the user.

In other embodiments, the system processor 1614 may execute instructions that implement a trained neural network or a machine learning algorithm to analyze/compare different settings to operator identification, patient identification, system location, time/day of the week, patient condition, etc. Accordingly, the ultrasound imaging system 100 can learn and implement specific device settings/configurations and/or user preferences for various different examinations/procedures. The machine learning algorithm can be an artificial neural network or deep learning algorithm that is trained to recognize patterns in the settings and the operating positions to the other additional factors.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code).

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on an imaging system having a display device, e.g., an LCD (liquid crystal display), LED (light emitting diode), or OLED (organic light emitting diode) monitor, for displaying information to the operator and a keyboard and a pointing device, e.g., a mouse or a trackball, by which the operator can provide input to the computer. In some implementations, a touch screen can be used to display information and to receive input from a user. Other kinds of devices can be used to provide for interaction with an operator as well; for example, feedback provided to the operator can be any form of sensory feedback, e.g., visual feedback, auditory feedback, or tactile feedback; and input from the operator can be received in any form, including acoustic, speech, or tactile input.

From the foregoing, it will be appreciated that specific embodiments of the technology have been described herein for purposes of illustration, but that various modifications may be made without deviating from the disclosure. Accordingly, the invention is not limited except as by the appended claims. Furthermore, certain aspects of the new technology described in the context of particular embodiments may also be combined or eliminated in other embodiments. Moreover, although advantages associated with certain embodiments of the new technology have been described in the context of those embodiments, other embodiments may also exhibit such advantages and not all embodiments need necessarily exhibit such advantages to fall within the scope of the technology. Accordingly, the disclosure and associated technology can encompass other embodiments not expressly shown or described herein.

We claim:

1. An ultrasound imaging system, comprising:
    a probe configured to send and receive ultrasound for performing a medical exam, a medical procedure, or both;
    a first display device coupled to the probe;
    a second display device coupled to the first display device;
    a first interface on the first display device to display images corresponding to received ultrasound signals;
    a second interface on the second display device to display the images corresponding to the received ultrasound signals, a graphic user interface (GUI), or both; and
    one or more processors operably coupled to the probe, the one or more processors configured to:
        select a mode of operation from a plurality of modes of operation of the ultrasound imaging system comprising a diagnostic mode that is used to perform the medical exam and a procedural mode that is used to perform the medical procedure based on a position of the first display device, wherein the first display device and the second display device operate to monitor a patient's tissue for the medical exam in accordance with the diagnostic mode when the first display device is at a first position relative to the second display device and wherein the first display device and the second display device operate to monitor an interventional instrument for the medical procedure in accordance with the procedural mode when the first display device is at a second position relative to the second display device, wherein the first position is associated with a first angle between the first display device and the second display device and the second position is associated with a second angle between the first display device and the second display device; and
        adjust one or more settings of the imaging system according to the mode of operation.

2. The ultrasound imaging system of claim 1, wherein the one or more processors are configured to adjust the one or more settings of a gain, a focal depth, a focal zone, a signal frequency depending on the mode of operation of the ultrasound system.

3. The ultrasound imaging system of claim 1, wherein the one or more processors are configured to adjust the one or more settings based on: for the procedural mode, enlarging one or more GUI control items, hiding one or more other GUI control items, increasing a separation distance between a set of the GUI control items, and enabling detection of inorganic material; and for the diagnostics mode, reducing a display size of the one or more GUI control items, enabling the one or more other GUI control items, and decreasing the separation distance between the set of the GUI control items.

4. The ultrasound imaging system of claim 1, wherein the one or more processors are configured to adjust the one or more settings based on: for the procedural mode, displaying the images including a scanned image continuously across the first interface and the second interface, or displaying a first image on the first interface and a second image on the second interface, wherein the first image and the second image highlight different characteristics of the received ultrasound signals; and for the diagnostics mode, displaying one or more images representing the received ultrasound signals on one of the first interface and the second interface, and displaying GUI controls, status information, or a combination thereof on the other of the first interface and the second interface.

5. The ultrasound imaging system of claim 1, further comprising:
    an orientation detection circuit operably coupled to the one or more processors, the orientation detection circuit configured to detect an operating orientation of the first interface, and the second interface.

6. The ultrasound imaging system of claim 5, wherein the orientation detection circuit includes one or more of an accelerometer, a gyroscope, a position encoder, a switch, and a camera.

7. The ultrasound imaging system of claim 1, wherein the first angle includes a first range of angles and the second angle includes a second range of angles.

8. The ultrasound imaging system of claim 7, the first range of angles including 0° to −15° from a horizontal plane, and the second range of angles including −55° to −90° from the horizontal plane.

9. An ultrasound imaging system, comprising:
a probe configured to send and receive ultrasound for performing a medical exam, a medical procedure, or both;
a first display device coupled to the probe;
a second display device coupled to the first display device;
a first interface on the first display device configured to display images corresponding to received ultrasound signals;
a second interface on the second display device configured to display the images corresponding to the received ultrasound signals, a graphic user interface (GUI), or both; and
one or more processors coupled to the probe, the one or more processors configured to:
select a mode of operation from a plurality of modes of operation of the ultrasound imaging system comprising a diagnostic mode that is used to perform the medical exam and a procedural mode that is used to perform the medical procedure based on a position of the first display device of the ultrasound imaging system, wherein the first display device and the second display device operate to monitor a patient's tissue for the medical exam in accordance with the diagnostic mode when the first display device is at a first position relative to the second display device, and wherein the first display device and the second display device operate to monitor an interventional instrument for the medical procedure in accordance with the procedural mode when the first display device is at a second position relative to the second display device, wherein the first position is associated with a first angle between the first display device and the second display device and the second position is associated with a second angle between the first display device and the second display device; and
adjust one or more settings of the imaging system according to the mode of operation based on: for the procedural mode of operation, enlarging one or more GUI control items, hiding one or more other GUI control items, increasing a separation distance between a set of the GUI control items, and enabling detection of inorganic material; and for the diagnostics mode, reducing a display size of the one or more GUI control items, enabling the one or more other GUI control items, and decreasing the separation distance between the set of the GUI control items.

10. The ultrasound imaging system of claim 9, wherein the one or more processors are configured to adjust the one or more settings of a gain, a focal depth, a focal zone, a signal frequency depending on the mode of operation of the ultrasound system.

11. The ultrasound imaging system of claim 9, wherein the one or more processors are configured to adjust the one or more settings based on: for the procedural mode, displaying processing results including a scanned image continuously across the first interface and the second interface, or displaying a first image on the first interface and a second image on the second interface, wherein the first image and the second image highlight different characteristics of the received ultrasound signals; and for the diagnostics mode, displaying one or more images representing the received ultrasound signals on one of the first interface and the second interface, and displaying GUI controls, status information, or a combination thereof on the other of the first interface and the second interface.

12. The ultrasound imaging system of claim 9, further comprising:
an orientation detection circuit coupled to the one or more processors, the orientation detection circuit configured to detect an operating orientation of the first interface and the second interface.

13. The ultrasound imaging system of claim 9, wherein the first angle includes a first range of angles and the second angle includes a second range of angles.

* * * * *